US 12,119,092 B2

(12) United States Patent
Bader et al.

(10) Patent No.: US 12,119,092 B2
(45) Date of Patent: Oct. 15, 2024

(54) PERIOPERATIVE EDUCATION AND ENGAGEMENT OF SURGICAL PATIENTS

(71) Applicant: KONINKLIJKE PHILIPS N.V., Eindhoven (NL)

(72) Inventors: Angela M. Bader, Chestnut Hill, MA (US); Adeel Yang, Chandler, AZ (US); Nasser Al-Sulaihim, Tempe, AZ (US); Anthony Monforte, Phoenix, AZ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 174 days.

(21) Appl. No.: 16/451,349

(22) Filed: Jun. 25, 2019

(65) Prior Publication Data
US 2019/0392922 A1    Dec. 26, 2019

Related U.S. Application Data

(60) Provisional application No. 62/689,653, filed on Jun. 25, 2018.

(51) Int. Cl.
*G16H 10/20* (2018.01)
*G16H 10/60* (2018.01)
(Continued)

(52) U.S. Cl.
CPC ............ *G16H 10/20* (2018.01); *G16H 10/60* (2018.01); *G16H 50/30* (2018.01); *G16H 20/10* (2018.01); *G16H 80/00* (2018.01)

(58) Field of Classification Search
CPC ........ G16H 10/20; G16H 10/60; G16H 50/30; G16H 20/10; G16H 80/00
See application file for complete search history.

(56) References Cited

U.S. PATENT DOCUMENTS

2004/0078227 A1* 4/2004 Morris .................. G06Q 10/10
                                                                    705/2
2005/0203773 A1   9/2005 Soto
                  (Continued)

FOREIGN PATENT DOCUMENTS

WO    WO-2019071185 A1 *  4/2019 ............. G16H 10/20

OTHER PUBLICATIONS

Lagoo-Deenadayalan, Sandhya A., Mark A. Newell, and Walter E. Pofahl. "Common perioperative complications in older patients." Principles and practice of geriatric surgery. Springer, New York, NY, 2011. 361-376. (Year: 2011).*

(Continued)

*Primary Examiner* — Mamon Obeid
*Assistant Examiner* — Chance L Smith

(57) ABSTRACT

When a patient is referred to a physician or hospital for a multi-encounter medical procedure, a computer retrieves information from a patient's electronic medical record (EMR) stored in an electronic medical record system of a medical facility. If the EMR suggests that the patient is possibly at risk, a computer poses a questionnaire to the patient, the questionnaire being specifically diagnostic for the suggested risk condition and/or appropriateness of care preferences of the patient. A computer evaluates the EMR information and questionnaire answers together to evaluate risk characteristics of the patient. Based on the evaluating, the computer recommends at least one pathway to be implemented by the medical staff in the patient's care.

16 Claims, 13 Drawing Sheets

(51) Int. Cl.
  *G16H 20/10* (2018.01)
  *G16H 50/30* (2018.01)
  *G16H 80/00* (2018.01)

(56) References Cited

U.S. PATENT DOCUMENTS

| | | | | |
|---|---|---|---|---|
| 2005/0273359 | A1* | 12/2005 | Young | G16H 10/20 |
| | | | | 705/2 |
| 2006/0015372 | A1* | 1/2006 | Graham | G06Q 10/06 |
| | | | | 705/3 |
| 2008/0059242 | A1* | 3/2008 | Stanford | G16H 10/60 |
| | | | | 707/999.107 |
| 2008/0208631 | A1* | 8/2008 | Morita | G16H 40/60 |
| | | | | 705/3 |
| 2010/0198755 | A1* | 8/2010 | Soll | G16H 10/60 |
| | | | | 706/11 |
| 2013/0073316 | A1* | 3/2013 | Miglietta | G16H 70/60 |
| | | | | 705/3 |
| 2013/0103414 | A1* | 4/2013 | Eng | G16H 50/30 |
| | | | | 705/2 |
| 2013/0132117 | A1* | 5/2013 | Barsoum | G16H 30/20 |
| | | | | 705/3 |
| 2015/0019259 | A1 | 1/2015 | Qureshi | |
| 2015/0213202 | A1* | 7/2015 | Amarasingham | G06F 19/00 |
| | | | | 705/2 |
| 2015/0310574 | A1* | 10/2015 | Williams | G16H 40/20 |
| | | | | 705/2 |
| 2016/0314279 | A1* | 10/2016 | Slepian | G06T 11/206 |
| 2016/0338685 | A1* | 11/2016 | Nawana | G16H 10/20 |
| 2017/0103189 | A1* | 4/2017 | Cott | G16H 40/63 |
| 2017/0147759 | A1* | 5/2017 | Iyer | G16H 10/20 |
| 2018/0052956 | A1* | 2/2018 | Sevenster | G16H 50/20 |
| 2019/0096509 | A1* | 3/2019 | Knoop | G16H 40/67 |
| 2020/0381127 | A1* | 12/2020 | Silverman | G16H 50/20 |

OTHER PUBLICATIONS

Blitz, Jeanna D., et al. "Preoperative evaluation clinic visit is associated with decreased risk of in-hospital postoperative mortality." Anesthesiology 125.2 (2016): 280-294. (Year: 2016).*

Carli, Francesco, and Celena Scheede-Bergdahl. "Prehabilitation to enhance perioperative care." Anesthesiology clinics 33.1 (2015): 17-33. (Year: 2015).*

Akiboye, Funke, and Gerry Rayman. "Management of hyperglycemia and diabetes in orthopedic surgery." Current diabetes reports 17.2 (2017): 13. (Year: 2017).*

Tobias, Joseph D. "Preoperative anesthesia evaluation." Seminars in Pediatric Surgery. vol. 27. No. 2. WB Saunders, Feb. 2018. (Year: 2018).*

* cited by examiner

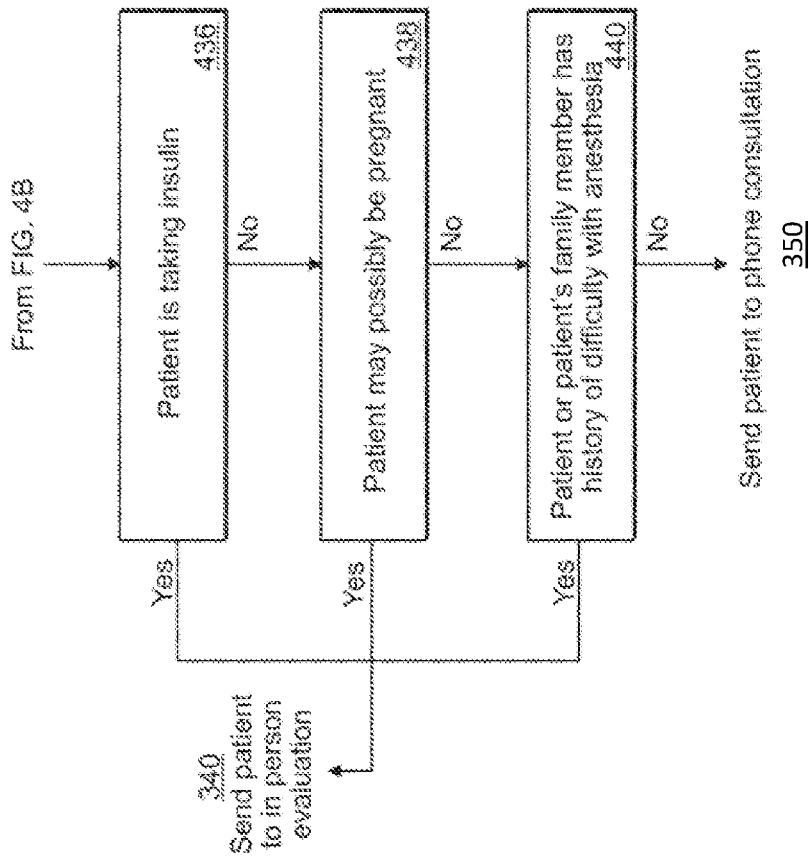

PERIOPERATIVE EDUCATION AND ENGAGEMENT OF SURGICAL PATIENTS

This application is a non-provisional of U.S. provisional application Ser. No. 62/689,653, filed Jun. 25, 2018, which is incorporated by reference.

BACKGROUND

This application relates to devices or appliance for use in operative surgery upon the body or in preparation for operative surgery, together with devices designed to assist in operative surgery.

SUMMARY

In general, in a first aspect, the invention features a method, and a computer with instructions for performance of the method. A computer retrieves information from a patient's electronic medical record (EMR) stored in an electronic medical record system of a medical facility. A computer obtains the patient's answers to questions of a questionnaire, the questions designed to identify risk characteristics of the patient and/or appropriateness of care preferences of the patient. A computer evaluates the EMR information and questionnaire answers together to evaluate risk characteristics of the patient and/or appropriateness of care preferences of the patient. A computer, based on the evaluating, recommends to medical staff of the medical facility, at least one pathway to be implemented by the medical staff in the patient's care, from among a library of templates of pathways, the pathways being standardized sets of tasks, medications, and/or interventions for an identified population of patients, each template pathway being neutral as to patient and schedule.

In general, in a second aspect, the invention features a method, and a computer with instructions for performance of the method. A memory of a computer stores a library of electronic templates of pathways for treatment of patients, each pathway being a standardized sets of tasks, medications, and/or interventions for an identified population of patients, each template pathway and template order being neutral as to patient and schedule. A computer receives an instruction from medical staff or a pathway-selection computer of a medical facility to select a pathway template from the library, and an identification of a patient. A computer instantiates the selected pathway and its orders as orders for the identified patient in a database of orders, and populating the instantiated orders with data to particularize the instantiated orders to the specific patient and the specific patient's medical condition, the data obtained by the computer in a query to an electronic medical record of the patient.

In general, in a third aspect, the invention features a method, and a computer with instructions for performance of the method. A computer assembles a database record in a patient electronic medical record (EMR) database, the record reflecting medical encounters of a patient and assembling them into a plurality of medical episode records for the patient, the episodes relating to corresponding medical conditions of the patient, each episode record storing information relating to care encounters of that episode relating to treatment of the corresponding condition. A computer stores the database record in a database of patient episode database, designed to permit longitudinal retrieval of encounters of an episode.

In general, in a fourth aspect, the invention features a method, and a computer with instructions for performance of the method. A computer automatically, in response to receiving a referral of a patient to a physician for a multi-encounter medical procedure, evaluates the patient's electronic medical record (EMR) for conditions suggesting the possibility of an at risk condition for the patient. In response to the EMR evaluation determining that the patient is possibly at risk, a computer poses a questionnaire to the patient, the questionnaire being specifically diagnostic for the at risk condition. A computer assesses the patient's answers to the questionnaire against criteria for the at risk condition. If the questionnaire assessment indicates the at risk condition for the patient, a computer proposes a pathway for the patient, the pathway chosen from among a library of templates of pathways based at least in part on the at risk condition assessed for the patient, the pathways being standardized sets of tasks, medications, and/or interventions for an identified population of patients, each template pathway being neutral as to patient and schedule.

In general, in a fifth aspect, the invention features a method, and a computer with instructions for performance of the method. As part of routine pre-surgical evaluation by a hospital, a computer poses a questionnaire to all patients for specified classes of procedures, the patients meeting specified criteria for risk of frailty, and obtaining patients' answers to questions of the questionnaire, the questions of the questionnaire designed to identify frailty of the patients. A computer evaluates the patients' questionnaire answers to evaluate frailty. If the questionnaire evaluating determines that the patient is likely frail, a computer recommends to medical staff at least one pathway relating to frailty to be implemented by the medical staff in the patient's care, from among a library of templates of pathways, the pathways being standardized sets of tasks, medications, and/or interventions for an identified population of patients, each template pathway being neutral as to patient and schedule.

In general, in a sixth aspect, the invention features a method, and a computer with instructions for performance of the method. A computer stores a library of electronic templates of pathways for treatment of patients, each pathway being a standardized sets of tasks, medications, and/or interventions for an identified population of patients, each template pathway and template order being neutral as to patient and schedule. As part of routine pre-surgical evaluation by a hospital, in response to receiving a referral of a patient to a physician for a multi-encounter medical procedure, a computer retrieves information from a patient's electronic medical record (EMR) stored in an electronic medical record system of a medical facility, and evaluating the patient's EMR for conditions suggesting the possibility of an at risk condition for the patient, at least one condition under evaluation being frailty. A computer assembles a database record in a patient EMR database, the record reflecting medical encounters of a patient and assembling them into a plurality of medical episode records for the patient, the episodes relating to corresponding medical conditions of the patient, each episode record storing information relating to care encounters of that episode relating to treatment of the corresponding condition. The database record is stored in a database of patient episode database, designed to permit longitudinal retrieval of encounters of an episode. In response to the EMR evaluation determining that the patient is possibly at risk, a computer poses a questionnaire to all patients for specified classes of procedures, the patients meeting specified criteria for possible risk, the questionnaire being specifically diagnostic for the at risk condition and/or appropriateness of care preferences of the patient, and obtaining the patient's answers to questions of the questionnaire. A computer evaluates the EMR information and questionnaire answers together to evaluate risk characteristics of the patient and/or appropriateness of care preferences of the patient. If the questionnaire assessment indicates the at risk condition for the patient, a computer recommends to medical staff, a pathway chosen from among the library. Based on the evaluating, a computer recommends to medical staff of the medical facility, at least one pathway from the library relating to the at risk condition to be implemented by the medical staff in the patient's care. A computer instantiates the selected pathway and its orders as orders for the identified patient in a database of orders, and populating the instantiated orders with data to particularize the instantiated orders to the specific patient and the specific patient's medical condition, the data obtained by the computer in a query to an electronic medical record of the patient.

Embodiments of the invention may include one or more of the following features. These features may be used singly, or in combination with each other. The risk characteristics identified by evaluating the EMR information and questionnaire answers may include frailty, anemia, diabetes, postoperative delirium, risk of extended inpatient rehabilitation or non-home discharge. The specified criteria for possible risk of frailty is an age of the patient. The questionnaire may poses at least four questions from the following list of seven questions, whether the patient has had a stroke or ministroke, whether the patient has chronic obstructive pulmonary disease, asthma, or another lung disease, whether the patient has had cancer, whether the patient has felt mostly tired in the last month, whether the patient has difficulty walking up 10 stairs without resting, whether the patient has difficulty walking a block, and whether the patient has unintentionally lost weight in the past 6 months. The specified criteria for possible risk of anemia may include lab results in the patient's EMR, and the pathway chosen from the library may be addressed to reducing risk of anemia in surgery. The specified criteria for possible risk of diabetes may be either an indication in the patient's EMR that the patient is on insulin, or that blood sugar levels are atypical, and the pathway chosen from the library may be addressed to reducing risk of diabetes during or after surgery. The possible risk may relate to the patient's mobility and abilities of independent living, and the pathway chosen from the library may be addressed to reducing risk in the patient's post-discharge living situation. The questionnaire may probe for an atypical risk preference of the patient. The computer may recommend pathways that include interviewing the patient and counseling for appropriate treatment; a recommendation as between an in-person preoperative evaluation versus a phone screen; pre-surgical prehabilitation to improve robustness in advance of surgery; The questions asked in the questionnaire may adapt, so that future questions to be asked of the patient are based at least in part on past questionnaire answers. The database record may be assembled from electronic medical record databases held at a plurality of hospitals or medical providers. The medical providers may use disparate EMR systems. Data copied from the hospital EMR databases may be normalized into a form for uniform storage at the database-assembly computer. The database may be assembled by creating a database of links to data stored at the hospital EMR databases. The database record may be assembled from electronic medical record databases held at a plurality of hospitals or medical providers.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION OF THE DRAWINGS

FIGS. 3, 4A-4C, 7A, and 7B are flowcharts.

DESCRIPTION

Figure 1:
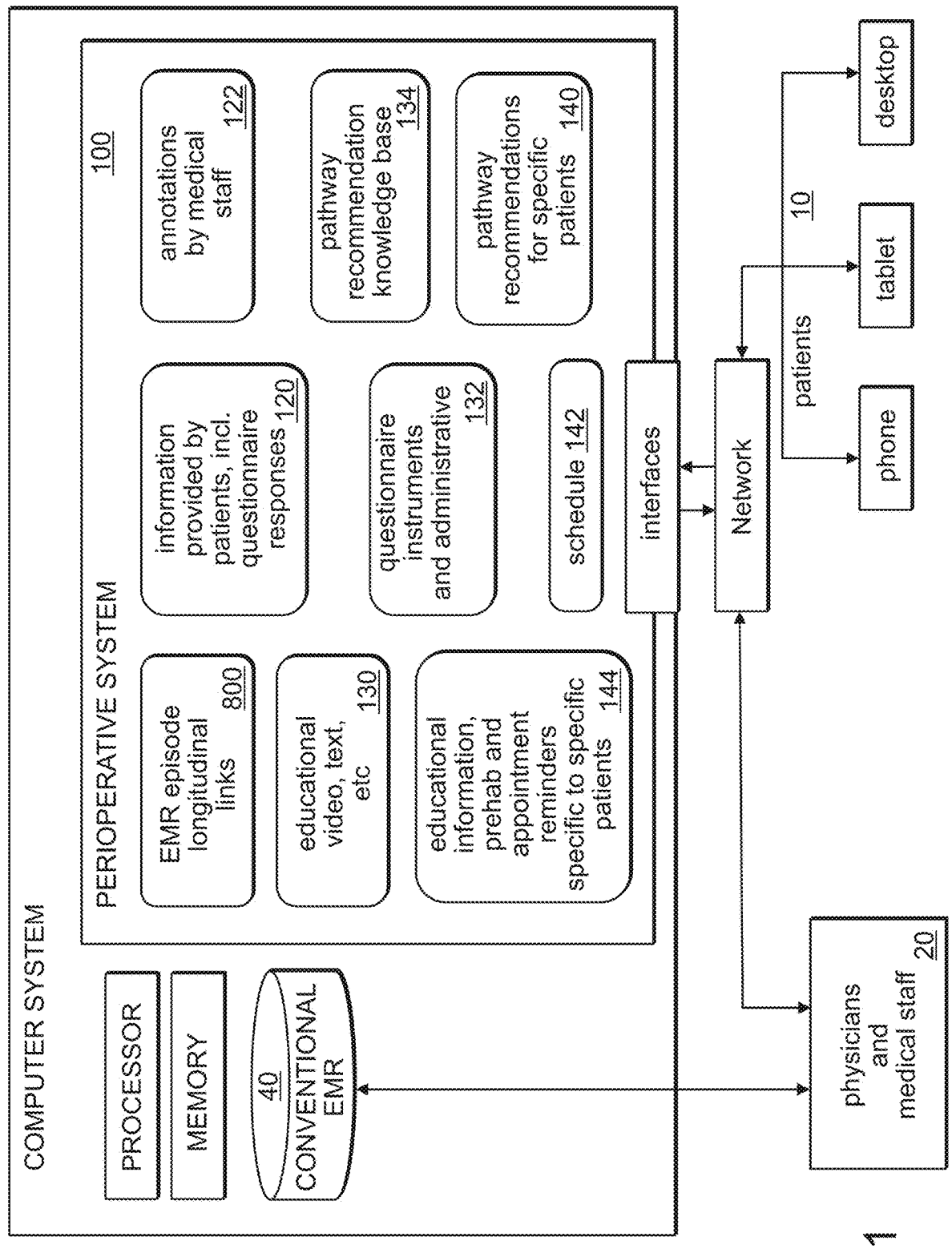
FIGS. 1, 2, 5, and 6 are block diagrams of a computer system.
Figure 2:
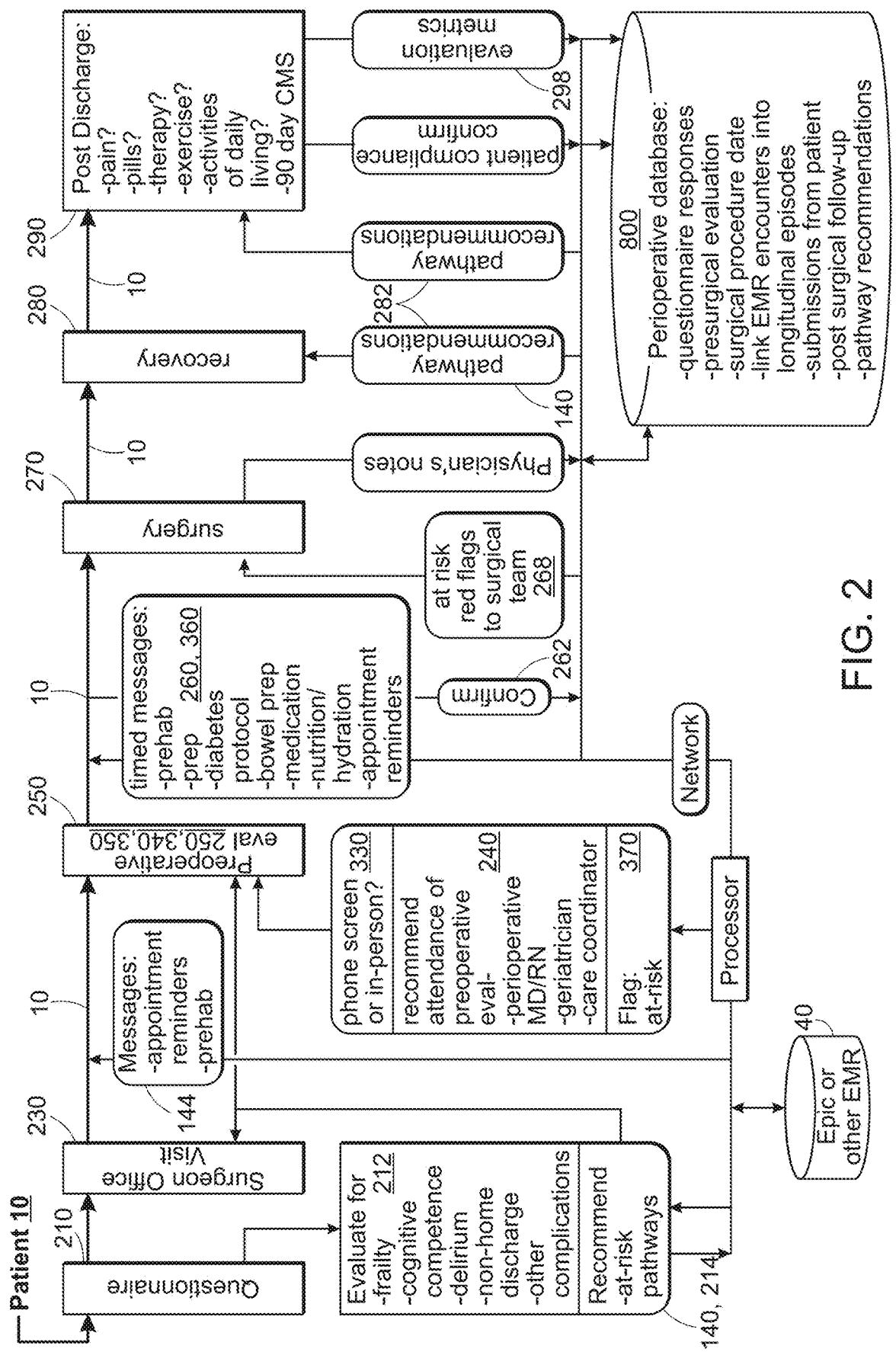

The Description is organized as follows.
I. Introduction and overview
II. System structure
   II.A. Perioperative database: linking encounters into longitudinal episodes, linking patients into populations
   II.B. Programs, modules, and data
   II.C. Medical staff and patient interfaces
III. Information capture, and issuing recommendations to patients and physicians
   III.A. Initial referral
   III.B. Initial questionnaire
      III.B.1.Surveys for frailty, dementia, risk of postoperative delirium, and other non-home discharge
      III.B.2.Adapting the questionnaire to the patient
      III.B.3. Other questions triggered by evaluation of the EMR
      III.B.4. Questions specific to the procedure
   III.C. Assisting patients and physicians in evaluating appropriateness of surgery
   III.D. Initial recommendations based on database 800 and questionnaire
   III.E. Surgeon's office visit
   III.F. Recommending pathways
   III.G. Improving fitness for surgery: education, prehabilitation and similar prep
   III.H. Preoperative preparation and evaluation
      III.H.1.Scheduling the preoperative evaluation visit: phone screen or live, and attendees
      III.H.2.Advance directives: healthcare proxy, living will, power of attorney
      III.H.3.The preoperative visit or phone screen
   III.I. Between the preoperative visit and the day of surgery: education and prehab
   III.J. The day of surgery
   III.K. Postoperative recovery, discharge, rehab, therapy, and follow-up
IV. Closing the loop: providing feedback to improve future health care
V. Computer implementation
   V.A. Network and communications connections
   V.B. Patient enrollment
   V.C. Reminders and notifications
   V.D. Patient timelines and perioperative database
   V.E. Other computer hardware concerns I. Introduction and Overview Referring to FIGS. 1 and 2, perioperative system 100 integrates information from an electronic medical record for a patient 10, survey responses from patient 10, and information from the physician and nursing staff 20. Perioperative system 100 may correlate this information and present it in a form to improve a patient's ability to make informed choices, improve sharing of decision making among patients and medical staff and the quality of decisions from that process, improve pre-surgical preparation and prehab, improve post-surgical care, and improve procedural feedback to allow future patients and physicians to incorporate more and better data into future decision-making Perioperative system 100 may integrate information starting from the time a patient is referred to a surgeon for surgery, through the ambulatory surgical visit, through hospitalization, through discharge, and as long as needed post-discharge, for at least the ninety days required for metrics required by CMS (Center for Medicare and Medicaid Services) and other payors. Improved integration of information and improved decision-making support at various points in the surgical pathway may improve the patient's and physician's decision-making in choosing among alternatives, improve outcomes, and reduce costs. Improved analysis may improve population management, improve the information available to support decision-making, and better group patients into a hospital's pathways of care. The use of perioperative system 100 to manage the process may provide providers with reminders of a wider set of options than can be brought to mind, and may enable the use of more complex perioperative pathways, more specifically tailored to the individual patient, compared to manual systems in which each decision has to be made as a one-off decision, and each decision and action has to be made and tracked manually. Perioperative system may provide a comprehensive flow management system, that covers most situations for most patients, and provides an end-to-end process, relieving physicians of one-off decision-making, in which each decision requires physician attention. Perioperative system 100 may be able to consider more variables and options, and offer different and more-detailed pathways than would be possible with a human operator. Perioperative system 100 may be useful in the context of surgery or other multi-encounter or complex medical condition.

Many current electronic medical record (EMR) systems 40 originated as billing systems. Because of that heritage, many current EMR systems 40 (for example, Epic®, from Epic Systems Corp. in Verona, Wisconsin; Cerner®, of North Kansas City, Missouri; Meditech from Medical Innovation Technology, Inc. of Westwood, Massachusetts; AllScripts Healthcare Solutions, Inc. of Chicago, Illinois; CPSI; and AthenaHealth, Inc. of Watertown, Massachusetts; and others) are structured around each patient encounter being a separate fee-for-service billable event. With minor exceptions (for example, labs are linked to a medical encounter), many modern EMR systems 40 do not naturally group patient encounters into longitudinal episodes of care, and do not naturally group patients with related conditions or appointments. In these systems, no encounter is linked with any other encounter, and the system maintains no longitudinal integration of information to track a patient's progress or cost through an entire care episode. Patients have no system access, and thus cannot provide information that gets linked into a longitudinal record of the entire episode without the physician having to provide a separate password to access the single datum from the patient. For example, if a surgical patient sees a geriatrician, EMR system 40 may file it as a geriatric visit rather than a surgical visit, and EMR system 40 may have no facility to link the two visits together. So physicians have to figure out by going into each individual chart what the patient has had done, and what the current status of each in-process episode may be. Perioperative system 100 may centralize the pertinent information and communication, and provide database annotations that link individual patient encounters in an encounter-based EMR system 40 into longitudinal episodes, which may improve care coordination, patient progress tracking, and cost tracking, which in turn may be especially valuable to a hospital that must identify specific costs in a bundled payment model.

Perioperative system 100 may improve patient engagement and access to information. Perioperative system 100 may provide patient 10 with a single portal to get information, to educate patient 10 and set expectations, for the medical team to obtain information from patient 10, for patient 10 to provide information to the medical team, to improve information available for discharge planning, for patient 10 and medical team to receive alerts, and for scheduling.

Perioperative system 100 may provide technological infrastructure to provide physicians and payors with an overview of a perioperative surgical episode as a whole. This may be especially important with bundled payment systems and accountable care organizations (ACOs), where a single payment must cover the cost of an entire episode, and the hospital or other provider is incentivized to minimize end-to-end costs. Perioperative system 100 may help hospitals 20 to track costs on an episode basis, and to provide the system-wide information that may help realign accounting and incentives that arise from silo'ed budgets and fee-for-service billing. Perioperative system 100 may facilitate population management (that is, standardizing care for all patients within a population set), which may in turn reduce over- and under-treatment. Perioperative system 100 may improve targeting of resources to the patients that need them, and to make better a priori decisions about which patient should have which surgery. Patients may be better prepared before surgery, and error may be reduced, which may reduce costly complications in the hospital 20 and after discharge.

Perioperative system 100 may record pertinent medical data at each step of the surgical process, including (but not limited to) requests made to technicians, post-op, blood bank, imaging, environmental systems, and transport. Perioperative system 100 may generate reports on specific steps or actions (actual surgery start time vs. patient in/out, operating room turnover time, anesthesia ready time, etc.) that may be broken down by time, location, personnel, department, and procedure type. In addition, perioperative system 100 may analyze the data it has collected to compute relevant performance metrics (e.g., top/bottom performers, workflow bottlenecks, and block time utilization), and report on outliers.

Perioperative system 100 may improve the ability of hospitals, government agencies, and payors to evaluate outcomes, at a group level and individual patient level, and connect output results to input decisions and actions. For example, perioperative system 100 may enhance the ability of a hospital 20 to evaluate whether an algorithm for deciding whether to involve a geriatrician before surgery is reducing complications and cost, because perioperative system 100 will continue to collect information throughout the perioperative episode, and to allow it to be correlated. Perioperative system may improve the ability of a hospital 20 to deliver value, where value is quality divided by cost.

II. System structure

II.A. Perioperative Database: Linking Encounters into Longitudinal Episodes, Linking Patients into Populations Perioperative system 100 may provide a database 800 that in turn provides links to link individual encounter records in EMR database 40 into a longitudinally-linked perioperative episode. The various linking records may be useful for cost analysis, outcomes research, reporting for public health or insurance or budgeting, etc. Perioperative database 800 may be formed either by creating "shadow copies" of the patient encounter data in the hospital's EMR database 40, or may be formed as "connective" records that indirectly link to records stored in the hospital's EMR database 40.

Perioperative database 800 may store the following kinds of data:

For a physician's day schedule, perioperative database 800 may allow delivery of a report that lists all patients to be seen for a day or session, with appointment time, age, type of surgery, surgeon, and flags 140, 214 for risk groups such as frailty, dementia, delirium, diabetes, anemia, and potentially other specific data that are highly relevant to this physician in this specific context. In contrast, EMR database 40 by itself may give only the list of patient names, with links to individual charts, but no way to consolidate the highly-relevant information into a report.

Perioperative database 800 may allow selection of subsets of a subset. For example, a physician may wish to see lists of, out of all patients to be seen today, the subset that are frail, and the subset that are at risk for delirium.

Some of these features exploit the structure of the questionnaire discussed below in § III.B.

Perioperative system 100 may also store the following data:

Information 120 provided by patients, including questionnaire responses, free text communications that patient 10 wishes to communicate to the surgical team, photographs provided by patient 10, and the like.

Annotations 122 to the medical record 40, 800 provided by physicians and other hospital staff that don't have a ready home location in the conventional EMR system 40.

Educational video, written materials, and the like 130 to be provided to patients Questionnaire instruments, and administrative software to control which questions are asked of which patients at what time 132.

A pathway recommendation knowledge base 134, which may include template orders for tests, procedures, therapy, etc. that can be ordered as a block package by a physician, and heuristics and other tests that perioperative system 100 may use to decide when to recommend a given pathway for a given patient at a given time to a given surgeon.

Scheduling information 142.

Reminders, messages, educational information, etc. selected out of the template base to be delivered to specific patients at specific times 144.

Pathway recommendations 140 for specific patients, as currently ordered by the physician.

A pathway or standard operating procedure may be a standardized set of tasks, medications, and interventions for a specific group of patients. A pathway provides a predictable clinical course, in which tasks, medications, and interventions are defined, optimized and sequenced, and tasks for the patient and multiple caregivers and the patient are specified and coordinated. A pathway may be organized by timeline, by day, by whether the care is to be delivered inpatient, outpatient, or home care. A pathway may range in scope from a simple medication script to a set of therapy steps for the patient to perform without direct supervision, to a comprehensive treatment plan. A pathway may have variances to adapt to individual patient conditions and preferences. Pathways evolve: as a medical facility gains experience with larger numbers of patients, the outcome data may be analyzed to identify alterations that may be used in a next application of the pathway. A pathway has usually been validated by evidence-based study and evaluation. Pathways are especially important when a given condition or pathology is common at a given institution, when that condition or pathology presents significant risks for patients, when the condition or pathology presents high costs for the hospital, when the clinical course is predictable and homogeneous care is more likely to be effective, when fully validated best practices exist, or when care is spread over a multidisciplinary team that must be coordinated.

II.B. Programs, Modules, and Data

Perioperative system 100 may have a number of modules and subprograms for functions such as interfacing with the pre-existing EMR database 40, obtaining patient answers to questionnaire 210, correlating data that exists elsewhere in the databases 40, 800 to develop recommendations for pathways 140, scheduling personnel at various meetings, surgery, and patient appointments 142; obtaining information from medical staff to annotate 122 the medical record; issuing educational materials to patient 10; allowing medical staff to adopt or amend pathways 140; and the like.

II.C. Medical Staff and Patient Interfaces

Perioperative system 100 may provides interfaces for patient 10, and medical staff 20 (including physicians, nurses, administrators, schedulers, etc.) in either a desktop/laptop "big screen" format, a mobile "small screen" format, a tablet "middle screen," or some combination thereof. Different persons may have different preferences.

Figure 3:
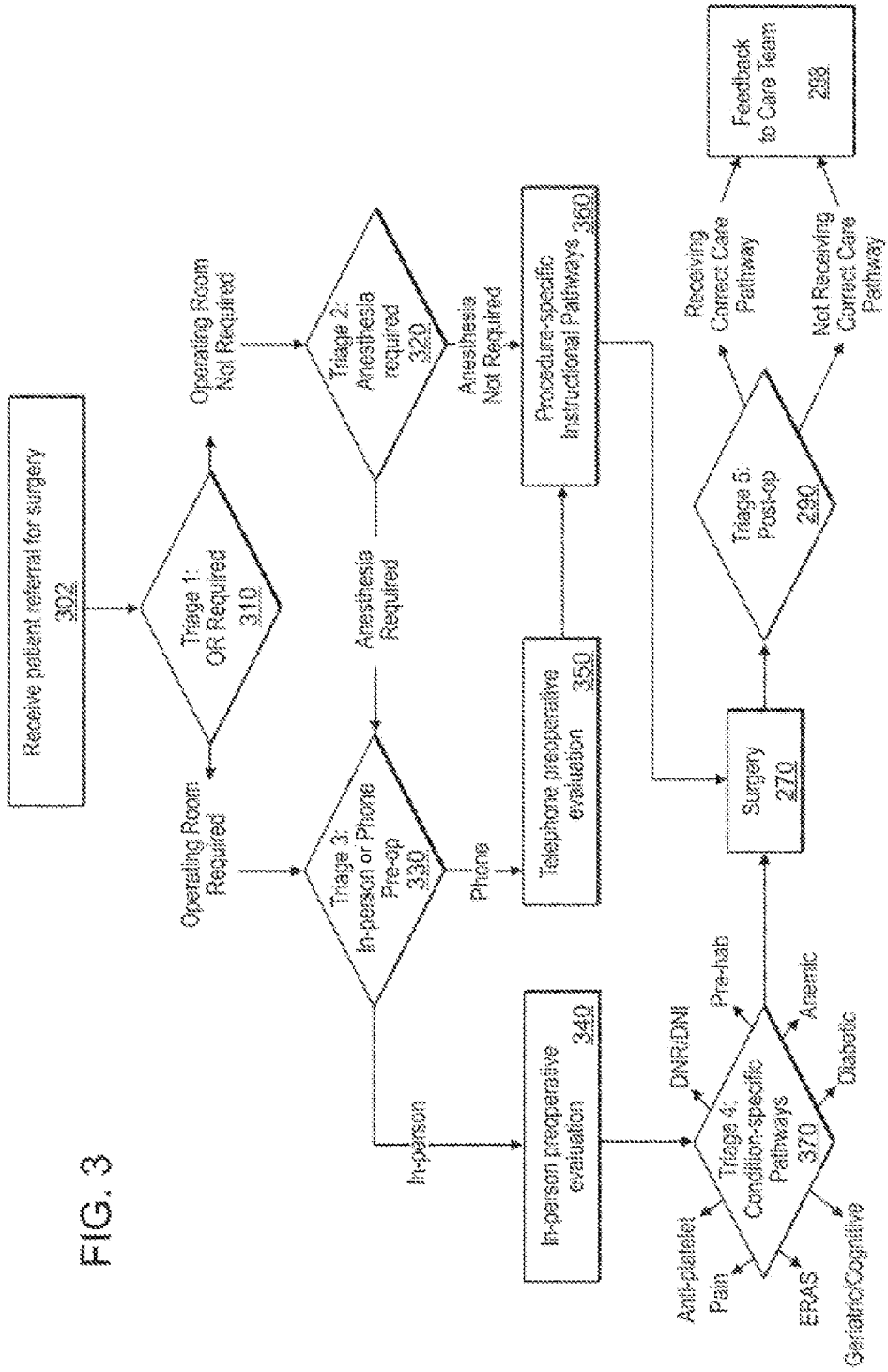

III. Information Capture, and Issuing Recommendations to Patients and Physicians III.A. Initial Referral Referring to FIGS. 2 and 3, when a patient is first referred for surgery (step 302), medical staff may create a record if a new episode in perioperative database 800. That new episode may trigger perioperative system 100 to query EMR system 40 for certain basic patient demographic and health information (as will be discussed below in connection with FIG. 6). The referring physician may enter information into a computer user interface indicating that patient 10 has been referred to surgery, and the type of surgery. EMR database 40 or perioperative database 800 may then store an indication that patient 10 has been referred to surgery and the type of surgery. Perioperative system 100 may perform a preliminary evaluation of the EMR for essentially every patient that enters the system, to screen for conditions that require further investigation.

III.B. Initial Questionnaire

Perioperative system 100 may send (step 210) a questionnaire to patient 10. In some designs of perioperative system 100, the questionnaire may be sent to essentially every patient scheduled for a presurgical clinic visit for given classes of surgery. In some cases, the specific questions sent to the patient may be determined, at least in part, by the initial preliminary evaluation of the EMR performed by perioperative system 100. In addition to the traditional questions to establish medical history and the like for the surgery itself, perioperative system 100 may ask a series of questions designed to predict needs and support decisions for each phase of the surgical episode:

suitability of this specific surgery for this specific patient.

whether patient 10 is a candidate for a telephone screen preoperative evaluation, or should come in for an in-person preoperative evaluation (step 330).

intensity of care: whether the procedure will likely require an operating room, and whether the surgery should be performed in a tertiary care hospital, a community hospital, or an affiliated surgery center (steps 310).

whether the procedure will likely to require anesthesia (step 320)

conditions that may affect recovery and/or post-discharge follow-up care

Each evaluation and recommendation 140 may take into account all the information gathered to date from the EMR 40, face-to-face interviews, and questionnaire 210, and this information may be used to tailor further questions to be asked by questionnaire module, depending on the information gained from the EMR 40. Earlier questions may be used to choose which questions to ask or not ask, or to tailor the wording of later questions.

Questions on questionnaire 210 may be structured for "yes/no" or checkbox answer, avoiding questions that ask for free text answers (or using free text only to elaborate yes/no/multiple-box questions). Questions with closed-form answer formats may improve the ability of a computer to automatically "score" patient 10 for various parameters, which may in turn allow for more targeted questioning, and improve the ability of a computer to automatically group patients into risk groups that call for specific surgical pathways.

Generally, it may be preferred to front-load the questions as early in the process as possible, for example, in this first questionnaire, rather than delaying them until a clipboard handed to patient 10 in the physician's waiting room. Patients are generally more comfortable answering questions in their homes (or the home of a relative) rather than in a physician's waiting room. A questionnaire before an office visit may contribute to delays in patient flow. Patients are more likely to answer questions completely and accurately if they have the freedom of time, which they're more likely to have at home than in a physician's waiting room. Elderly patients and children are more likely to respond completely and accurately if they can enlist the help of a relative or a phone support person, especially if patient 10 has failing vision or mental state. Perioperative system 100 may notify the physician's staff if patient 10 is delayed in answering questionnaire 210, especially as the date for the ambulatory evaluation visit (see section III.E) approaches.

Patient 10 may indicate whether they prefer future information to be communicated by phone, email, text, or other medium.

Perioperative system 100 may pose questions to patient 10 through a user interface on the patient's home computer or smartphone, or at a computer in the physician's office (though, as noted, this is generally less preferred). As patient 10 provides answers to the questions, perioperative system 100 may store the answers in perioperative database 800.

III.B.1. Surveys for Frailty, Dementia, Risk of Postoperative Delirium, and Other Non-Home Discharge Questionnaire 210 may include questions 212 to assess for certain at risk groups, such as frailty, preexisting dementia, postoperative delirium, and other non-home discharge conditions. In some cases, validated and evidence-based questions and survey methods may exist; in other cases, the questions may be experimental or "best guess" to try to identify at risk patients.

A generalized risk assessment questionnaire may ask questions such as the following, and the answers may be scored as indicated:

1. What is your age? (50-65, 2 points; 66-75, 1 point; >75 0 points)
2. What is your gender? (male, 2 points, female 1 point)
3. How far on average can you walk? (two blocks or more, 2 points; 1-2 blocks, 1 point; housebound, 0 points)
4. Which gait aid do you use (more often than not) (none, 2 points, single-point stick, 1 point, crutches, frame, walker, 0 points)
5. Do you use community supports such as home help, meals on wheels, district nursing, etc. (none or one per week, 1 point; two or more per week, 0 points)
6. Will you live with someone who can care of you after your operation (yes, 3 points; no 0 points)

Scores May be Predictive as Follows:

Score <6 may be predictive of extended inpatient rehabilitation

Scores 6-9 may be predictive that patient 10 may be discharged to home, if additional intervention can be arranged Scores >9 may be predictive that patient 10 is likely to be discharged directly to home Overall risk of non home discharge and for frailty may be evaluated by a questionnaire such as the following. The choice of which questions to ask may be based on demographic information pulled from the patient's EMR. For example, a frailty assessment may be posed to all patients that are over 70 years old. The patient's EMR may indicate the patient's primary language; perioperative system 100 may pose the questions in that primary language. The questions may be posed to the patient in the patient's own home, or to be completed with whatever assistant is most comfortable for the patient. A non-home discharge and frailty questionnaire may be posed as follows:

1) How old are you? (Age <50=4 points; Age 50-59=5 points; Age 60-70=7 points; Age 71-80=17 points; Age >80=27 points)
2) Your gender? (Male=0 points; Female=4 points)
3) Will you live with someone who can care for you after your operation? (No=7 points)
4) How tall are you?
5) How much do you weigh? (from questions 4 and 5, calculate body mass index. If BMI >35, =6 points)
6) Have you ever had a stroke or mini-stroke? (Yes=6 points, plus see frailty score)
7) Have you ever had a heart attack? (see frailty score)
8) Have you ever had heart failure? (see frailty score)
9) Do you have high blood pressure? (see frailty score)
10) Are you on kidney dialysis? (Yes=12 points, plus see frailty score))
11) Do you have diabetes? (see frailty score)
12) Do you have peripheral vascular disease in your arms or legs? (see frailty score)
13) Do you have COPD, asthma, or another lung disease? (Yes=4 points, plus see frailty score)
14) Do you have an alcohol or drug problem? (Yes=11 points)
15) Do you have a problem with anxiety, depression or other similar issue? (Yes=5 points)
16) Do you have arthritis? (see frailty score)
17) Do you have cancer—not a skin cancer? (see frailty score)
18) Have you felt mostly tired in the last month? (see frailty score)
19) By yourself, and not using aids, do you have any difficulty walking up 10 stairs without resting? (see frailty score)
20) By yourself, and not using aids, do you have any difficulty walking a block? (see frailty score)

21) Have you unintentionally lost weight in the past 6 months? (see frailty score)
22) Have you ever had heart surgery? (Yes=3 points)
23) Which gait aid do you use (more often than not)? (None=0 points, cane=2 points, crutches/walker=5 points, wheelchair=6 points)
24) Do you use any community supports (Home health aide, meals on wheels, Visiting Nurse)? (None or once per week=0 points, Two or more per week=5 points)

From this Survey, a Frailty Score May be Computed as Follows:
Questions 6, 7, 8, 9, 10, 11, 12, 13, 16, 17 count each Yes answer. If more than 5, =1 point.
Question 18. Yes=1 point
Question 19. Yes=1 point
Question 20. Yes=1 point
Question 21. Yes=1 point Frailty Score Assessment:

| Score = 0 | Robust |
| Score = 1-2 | Pre-Frail |
| Score = 3-5 | Frail |

Some of these questions may also be predictive of post-surgical delirium.

Figure 4A:
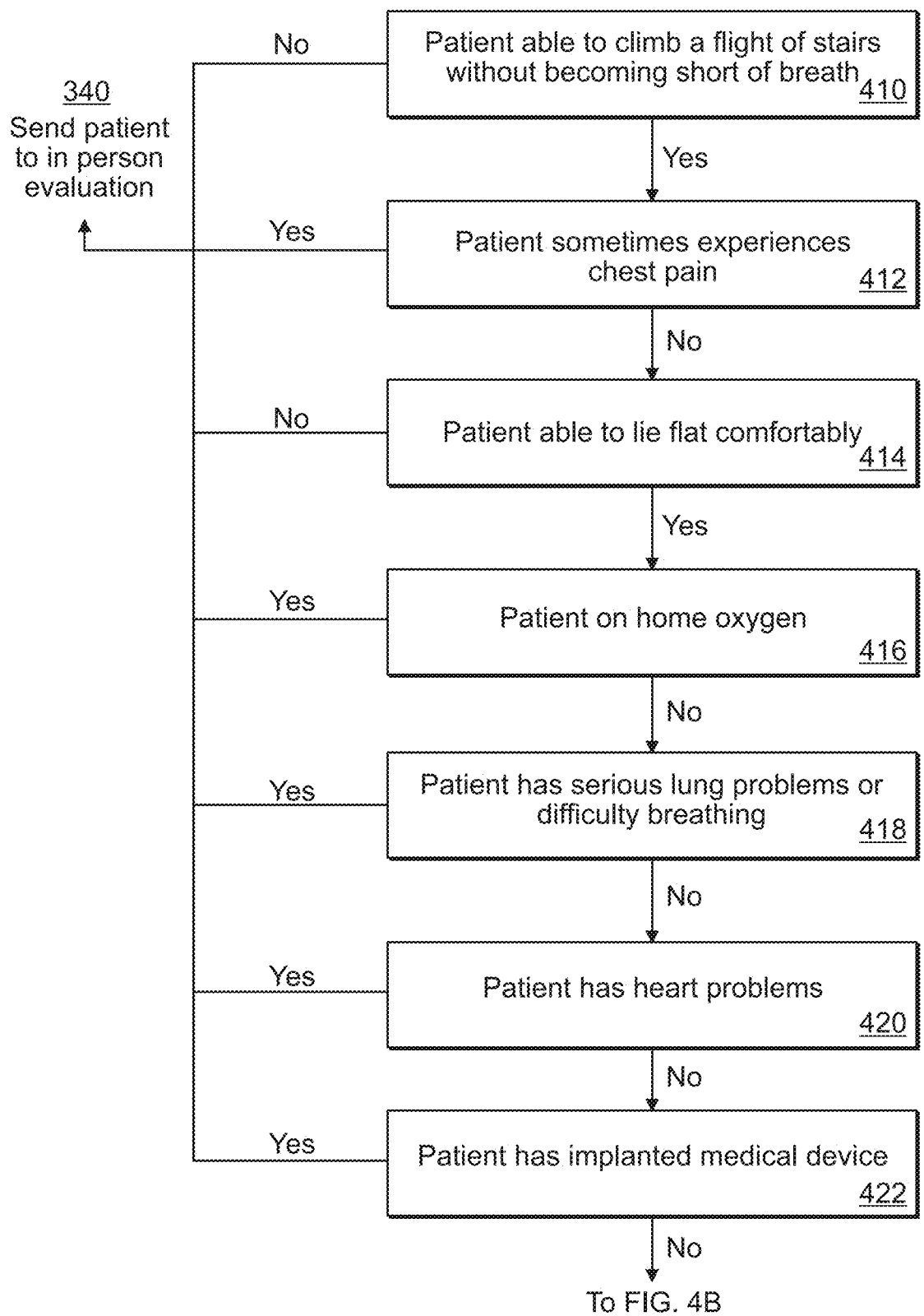
Figure 4B:
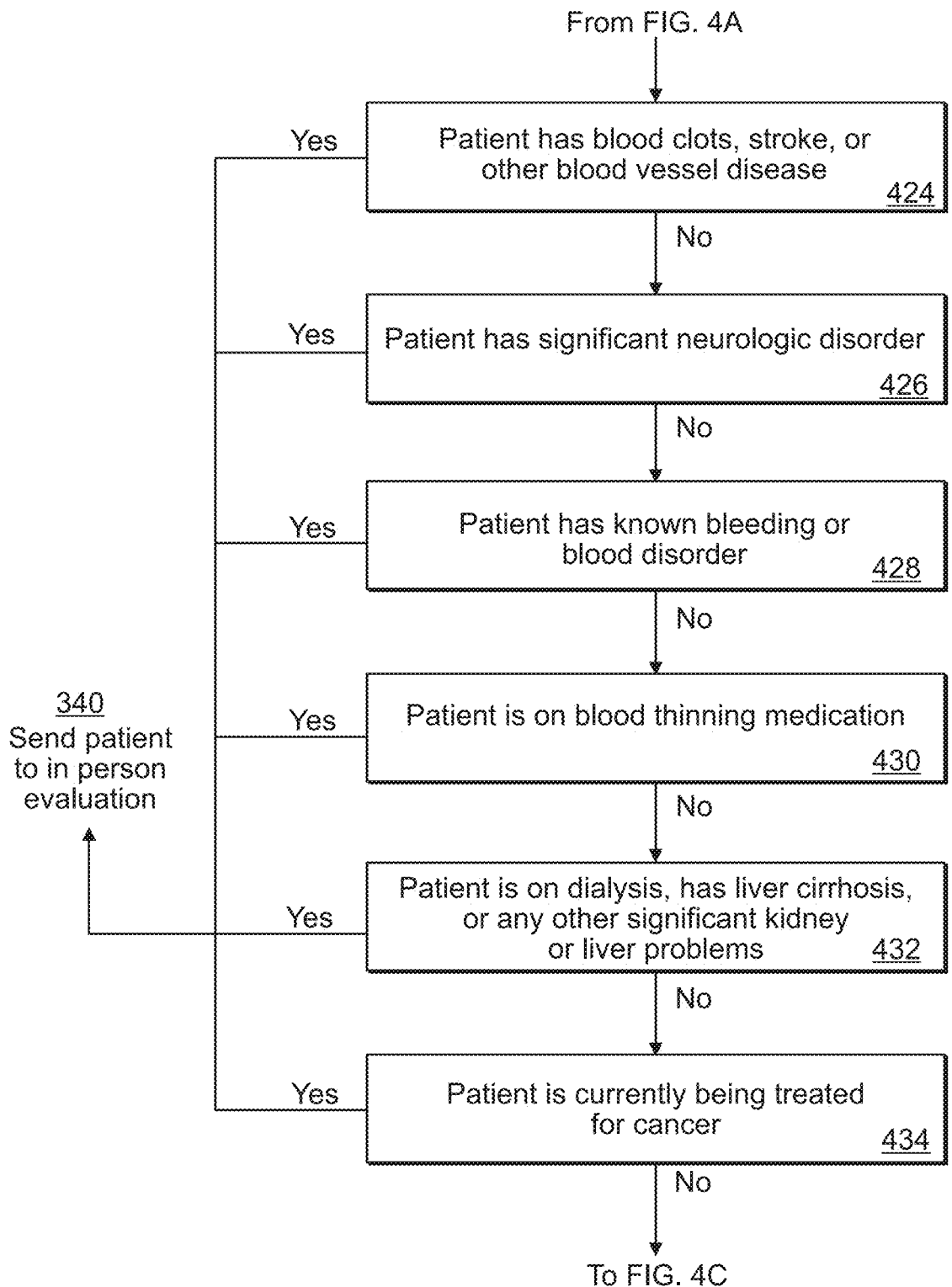

Referring to FIGS. 4A, 4B, and 4C, perioperative system 100 may ask the following questions. An adverse answer to any single one may indicate that patient 10 must have an in-person preoperative evaluation, rather than a phone screen (as discussed in § III.H.1, below).
1. Are you able to climb a flight of stairs without being short of breath (step 410)?
2. Have you ever experienced chest pain (step 412)?
3. Are you able to lie flat comfortably (step 414)?
4. Are you on home oxygen (step 416)?
5. Do you have serious lung problems or difficulty breathing (step 418)?
6. Have you had any heart problems, for example, heart attack, heart surgery, placement of a heart stent, atrial fibrillation, congestive heart failure, and so on (step 420)?
7. Have you had any implanted medical devices, such as a pacemaker, ICD/defibrillator, insulin pump, LVAD, or vagal nerve stimulator (step 422)?
8. Have you had any blood clot, stroke, or any serious disease of the blood vessels, for example, carotid disease, peripheral vascular disease (step 424)?
9. Have you had any significant neurologic disorder, for example, epilepsy, ALS, and so on (step 426)?
10. Do you have a known bleeding or blood disorder, for example, hemophilia, sickle cell disease, etc. (step 428)?
11. Are you on any blood thinning medication, for example, Heparin, Coumadin, Plavix, Pradaxa, or Xaralto (step 430)?
12. Are you on dialysis? Do you have liver cirrhosis, or any other significant kidney or liver problems (step 432)?
13. Are you currently being treated for cancer (step 434)?
14. Are you taking insulin (step 436)?
15. Could you possibly be pregnant (step 438)?
16. Have you or any family member have a history of difficulty with anesthesia (step 440)?

If all of these questions are answered with the "robust" answer, then patient 10 may be eligible for a phone screen (step 350) instead of an in-person preoperative visit (step 340) (see § III.H.3, below). That recommendation 140 may be stored in perioperative database 800.

Similar questionnaires may be developed to identify similar at-risk populations. The software for the questionnaire and consequent recommendations may be designed to accept the survey, its scoring algorithm, and a template pathway of template orders, and blank-filled open template variables (see discussion of "content resolver" 520 in § V.A, below) as parameterized "macro" inputs. This may permit easy addition of new questionnaires, and new pathway templates to be instantiated into the patient's medical record when the patient's answers trigger some action.

III.B.2. Adapting the Questionnaire to the Patient

Returning to FIGS. 2 and 3, the course of questions to be asked by perioperative system 100 may be tailored to the specific surgery, the specific surgeon, information obtained from EMR 40, and answers to earlier questions on questionnaire 210.

In some cases, the questions and scoring of questions may adapt based on information about patient 10. For example, an opioid risk questionnaire might ask questions whose scoring adapts based on whether patient 10 is male or female:

| Mark each box that applies | Female | Male |
|---|---|---|
| Family history of substance abuse | | |
| Alcohol | 1 | 3 |
| Illegal drugs | 2 | 3 |
| Rx drugs | 4 | 4 |
| Personal history of substance abuse | | |
| Alcohol | 3 | 3 |
| Illegal drugs | 4 | 4 |
| Rx drugs | 5 | 5 |
| Age between 16-45 years | 1 | 1 |
| History of preadolescent sexual abuse | 3 | 0 |
| Psychological disease | | |
| ADD, OCD, bipolar, schizophrenia | 2 | 2 |
| Depression | 1 | 1 |
| Scoring totals | | |

III.B.3. Other Questions Triggered by Evaluation of the EMR

Other conditions discernable from the medical record that may trigger specific questions or pathways include the following:
Anemia may be identified in the medical record by lab results. If anemia is identified, the patient may be asked whether the patient has had a blood transfusion in the past, and in the recent past. The patient may be asked whether the patient is currently on an iron supplement. Depending on the answers and nature of surgery, a pre-operative iron transfusion may be added to the patient's pathway or medical orders.
Diabetes may be identified in the medical record based on lab results, or a prescription for insulin. If diabetes is identified, then the questionnaire may ask what medications the patient is on, and range of morning blood glucose. Oral diabetes medications will have to be stopped for some time after surgery, so an alternative medication regime must be put in place. If blood glucose is not being well controlled, the patient will require a diabetes care pathway.
A history of mobility issues, or a referral for hip or knee surgery, may trigger questions that inquire into the patient's home (is there a stairway), other people at home, a home nursing aide, and the like.

III.B.4. Questions Specific to the Procedure

Questionnaire 210 may include questions tailored to specific procedures. The set of questions asked to any particular patient will likely vary, depending on the information gathered from the EMR 40, and answers to earlier questions will alter the set of later questions to be asked.

Questionnaire 210 may ask questions to establish suitability of a specific surgery course, to help choose from among surgical alternatives, and to ensure that the right patient is getting the right surgery, and to help establish reasonable expectations. For example, questionnaire 210 may ask:

What is the patient's level of function at some time in the past?

What activities of daily life are most affected by the illness/disease?

Questionnaire 210 may ask about specific tradeoffs that may face patient 10—for example, side effects of prostate surgery can be significant, and the relevance of those potential side effects will vary patient-to-patient.

Perioperative system 100 can ask questions that help patient 10 understand all these issues, and gather preferences from patient 10 that may help the physician understand what factors are most important to this specific patient, so that sound and educated risk tradeoffs can be made.

III.C. Assisting Patients and Physicians in Evaluating Appropriateness of Surgery Difficult questions arise as to appropriateness of care, especially when a patient is in the last year of life. Appropriateness is often entirely the subjective evaluation of patient 10, and that subjective evaluation may be entirely different than conventional medical definitions of "success." For example, one patient may be in such pain that patient 10 considers high risk of morbidity and mortality to be acceptable. Another patient may choose to accept the pain when educated on the risk. Clinicians may not be attuned to achieving patient 10's objectives. Resolving these deeply personal issues, and coming to agreement on the definition of "success" and "appropriate care" requires a level of conversation that is not common in medicine. Perioperative system 100 may assist in identifying situations where the medical team must make an extra effort to understand the patient's objectives, and where patient 10 may require careful counseling to understand risks and outcomes.

After a patient is referred for surgery, perioperative system may ask the referring physician or the patient's primary care doctor a few questions to ascertain whether patient 10 may have an atypical outcome preference. In some cases, a questionnaire to these physicians may be as simple as one or two questions:

If this patient died within the next year, would you be surprised?

Has a discussion occurred to ensure that the patient's goals and values are aligned with the expectations for potential risks and benefits of the procedure?

If the "surprise" question is answered "no" or the "discussion" question is answered "no" or the frailty or cognitive impairment evaluations suggest that patient 10 may need additional counseling, then perioperative system 100 may alert patient 10 and to the hospital's hospitalist or perioperative team that perioperative appropriateness and counseling appointment may be helpful, either before the first meeting with the surgeon, or with the hospitalist/perioperative physician attending the first meeting with the surgeon, or shortly after the first meeting.

III.D. Initial Recommendations Based on Database 800 and Questionnaire

Based on the EMR 40 and questionnaire 210, perioperative system 100 may develop and record certain initial estimations of at risk issues for patient 10, and offer recommendations for pathways 140. These at risk categorizations 214 and recommendations 140 may be offered to patient 10 and medical staff at relevant stages of the care episode.

Once the surgeon knows that patient 10 is frail, there may be certain things that prehabilitation can do to improve this patient's outcome. For example, for a patient known to be frail, the surgeon might decide to delay the surgery for 30 days to build up their nutrition or respiratory function. For a frail patient, the surgeon may bring in a geriatrician, care coordination nurse, nutritionist, physical therapist, and the like, and a frail patient may require an extra evaluation by an anesthesiologist. Determination that patient 10 is frail may affect the booking date for surgery, preoperative prehabilitation, and the like.

The most common surgical complication is post-operative delirium. One case of delirium costs between $15,000 and $60,000, and delirium often leads to prolonged and sometimes unrecoverable cognitive dysfunction. Questionnaire 210 may include questions to identify risk of delirium. Some questions relevant to frailty (see section III.B.1) may also be predictive of risk factors for delirium. The report generated by perioperative system 100 may report "at risk delirium, yes, no."

Similarly, mental competency and cognitive impairment may affect the choice of surgical pathway. Surgery is far more likely to be successful if patient 10 can participate in decision making, can understand the likely complications and tradeoffs, and can fully engage in prehabilitation and postoperative therapy. But a patient of compromised mental competency cannot give truly informed consent, nor can such a patient participate in the pre-surgical and post-surgical therapy that may be essential to a favorable outcome. Thus, perioperative system 100 may include an evaluation for mental competency. If patient 10 doesn't timely complete questionnaire 210, and does not complete it after some number of follow-up phone calls, that noncompliance may be an indicator that patient 10 is at high risk of being cognitively impaired.

In each case of at risk condition, perioperative system 100 may flag the patient's record to indicate the risk, for example, that patient 10 is frail, demented, at risk for cognitive impairment, delirium, diabetes, anemia, or other risk categories, or that patient 10 may require pathways for anti-platelet, pain, ERAS (enhanced recovery after surgery), or has DNR (do not resuscitate) or DNI (do not intubate) instructions in place. Based on the information obtained from medical record 40, questionnaire 210, and any other clinical information, perioperative system 100 may compute an initial recommendation whether to use a phone screen for a preoperative evaluation or an in-person evaluation, and for any condition-specific preoperative pathway, and note those recommendations in perioperative database 800. Similarly, perioperative system 100 may recommend 140 involvement of a geriatrician and/or care coordination nurse.

If the surgery if for an urgent or rapidly progressing condition, then delay and prehabilitation may not be indicated.

III.E. Surgeon's Office Visit

To prepare the surgeon for a day of presurgical office visits (step 230), perioperative system 100 may provide a report 370 that gives certain population management indicators for the day's patients. The report may indicate which patients are frail, which are at high risk for cognitive impairment, which are at high risk for delirium, which are at high risk for non-home discharge, and which are robust.

This report may assist the surgeon and patient to cooperatively decide whether or not to do surgery at all, and to plan various pathways.

If patient 10 was initially evaluated for a phone screen for preoperative evaluation and the surgeon's office visit turns up further concerns that warrant in-person evaluation, the surgeon can change this indication in the record maintained by perioperative system 100 from phone screen to in-person preoperative evaluation.

III.F. Recommending Pathways

Perioperative system 100 may automatically recommend 140, 214 preoperative and postsurgical pathways based on the EMR 40, questionnaire, and information obtained in office visits:

What surgical procedure will be performed?
Can patient 10 be evaluated by phone screen, or is an in-person evaluation warranted?
Will the procedure require an operating room?
Will the procedure require anesthesia? What kind?
Should any pathways be added to the orders for this patient? For example, one order set might be a delirium prevention pathway. Other potential pathways that might be discernable from the information available to perioperative system 100 and to the physician include pathways for Enhanced Recovery After Surgery (ERAS), geriatric/cognitive care, diabetic care, anemia, pain, anti-platelet, special issues such as Do Not Resuscitate or Do Not Intubate, pre-habilitation, and others.

After the surgeon's visit, the surgeon may review recommendations made by perioperative system 100 based on the surgeon's human judgement. The surgeon may adopt any recommendation offered by perioperative system 100, amend the recommendation, or replace it entirely with orders entirely at the surgeon's judgement. The surgeon may issue an order set 140 specific to that risk, and tailored to patient 10, which overrides any initial recommendation suggested by perioperative system 100.

III.G. Improving Fitness for Surgery: Education, Prehabilitation and Similar Prep Based on the information available to it, and at the direction of medical staff, perioperative system 100 may send educational notifications 260, 360 to patients 10. For example, patients scheduled for knee surgery may receive a video explaining the surgery, risks, expected recovery and improvement, and the importance of post-surgical physical therapy.

In some cases, it may be desirable for patient 10 to engage in some pre-surgical prehabilitation or prep. For example, some patients may desirably obtain physical therapy, change medication, change diet, or other change of behavior to improve fitness for surgery. Perioperative system 100 may provide patient 10 with education to assist patient 10 in complying with these pre-surgical instructions, for example, as an instructional video. Perioperative system 100 may follow-up with texts or email messages 260 to remind patient 10, and may request that patient 10 confirm 262 completion of the pre-surgical instruction by checking a box, returning a text, or otherwise.

III.H. Preoperative Preparation and Evaluation

III.H.1. Scheduling the Preoperative Evaluation Visit: Phone Screen or Live, and Attendees As discussed in § III.B above, the initial questionnaire 210 may identify whether patient 10 is in any of the at risk categories that call for an in-person preoperative visit, or whether preoperative evaluation can be conducted via a phone screen. Likewise, during the surgeon's office visit, further information may come to light that raises of questions of risk that should be evaluated in an in-person preoperative visit, rather than a phone screen, and medical staff may update the recommendation stored in the perioperative database 800.

Based on questionnaire 210 and surgeon's impression from the office visit, perioperative system 100 may recommend attendees for the preoperative evaluation visit. For example, for a patient at risk for dementia or frailty, perioperative system 100 may recommend that a geriatrician attend. For a patient with dementia, frailty, risk of delirium, or other non-home discharge, perioperative system 100 may recommend that a care coordination nurse attend.

III.H.2. Advance Directives: Healthcare Proxy, Living Will, Power of Attorney

Perioperative system 100 may send patient 10 a set of questions relating to advance directives such as a healthcare proxy, a living will, a healthcare power of attorney, and the like. This is quite time consuming when done in the hospital, and patient 10 can generally make better decisions if those decisions are made in the patient's own home (or at the home of a relative) in consultation with family members.

Perioperative system 100 may ask whether the patient has these advance directives in place, and if so, to upload them so that they can be in the hospital's possession as surgery begins. If they are not in place, perioperative system 100 may send out videos or other instructional material explaining why these documents should be in place, who can be the patient's health care proxy, how to choose from among several form directives, and how to properly execute them and ensure that copies are filed where they will be available to the people that need them.

If patient 10 has designated a healthcare proxy, perioperative system 100 may inquire to ensure that patient 10 has discussed the patient's wishes and goals with that proxy.

A value indicating whether patient 10 was referred to an in person preoperative evaluation or a telephone screen preoperative evaluation may be stored in perioperative database 800 or in the patient's EMR 40 or both. Perioperative system 100 may direct patient 10 to an in-person preoperative evaluation or to a telephone preoperative evaluation by displaying a notification to patient 10 on a computer or smartphone screen, or hospital staff may schedule the evaluation by phone.

III.H.3. The Preoperative Visit or Phone Screen

For patients identified at being at risk, perioperative system 100 may schedule patient 10 for a preoperative phone screen or in-person visit 250 a few days before the surgery is scheduled.

Perioperative system 100 may recommend 240 staff to attend the preoperative visit. The default attendance includes patient 10 and a perioperative physician or nurse. Perioperative system 100 and/or medical staff may recommend further attendees, such as a geriatrician, a care coordination nurse, or other staff to provide evaluation of and advice to patient 10.

At the preoperative visit 250, perioperative system 100 may survey patient 10 for the following, or prompt the perioperative physician/nurse to probe the following:

Should patient 10 not be cleared for surgery at all?
Has patient 10 complied with presurgical prehab preparations? To what degree?
Do any of the patient's medications present risks for surgery (for example, blood-thinners should be stopped before surgery)?

Has the patient's medication changed? Do any current medications present risks?

Has patient 10 completed all applicable advance directives? Does patient 10 have questions about any advance directive? Does patient 10 fully understand what they mean? Has patient 10 discussed goals with the designated proxy? Video may be helpful to educate patient 10.

Does patient 10 have any other condition that calls for careful management, either before, during, or after surgery?

Perioperative system 100 may recommend diet, medication, exercise, and the like for the days remaining until surgery.

If patient 10 is identified as belonging to an at risk population, perioperative system 100 may have a pathway to recommend 140, including some behavioral or medication change for patient 10, and affiliation of another physician.

Perioperative system 100 may propose further recommended pathways or interventions based on the new information gathered in the preoperative visit. Medical staff, again, have options to adopt any recommendation offered by perioperative system 100, amend the recommendation, or replace it entirely with orders entirely at medical judgement. Medical staff issue an order set specific to that risk, and tailored to patient 10, and add that to either the EMR medical record 40 or to perioperative database 800.

III.I. Between the Preoperative Visit and the Day of Surgery: Education and Prehab Between the preoperative visit and surgery it may be very important to provide patient 10 with education materials. This education may be most effective if delivered on a time schedule. For example, before gastrointestinal or abdominal surgery or colonoscopy, education materials, reminders for diet, laxatives, and the like may be delivered 260 electronically at the time patient 10 is to act. For orthopedic surgery, perioperative system 100 may provide patient 10 with videos to instruct on a prehabilitative exercise regimen, with timed reminders to do the exercises. This timed electronic delivery may be far more effective than a packet of papers delivered all at one time. Perioperative system 100 may provide patient 10 with a box to check off to confirm 262 that the drugs, diet, exercise, etc. instructions have been carried out, and this checkoff may improve compliance. Targeted electronic messages may result in improved throughput at the surgical facility and reduction in postoperative infection, because of reduction in incomplete bowel preparation, failure to take the right medication at the right time, and patients failing to arrive on time. Timed delivery may be especially valuable for elderly patients.

Perioperative system 100 may use the information it has collected from the patient's EMR 40, from questionnaire 210, from the surgeon, and from the preoperative evaluation to compute recommendations and reports. For example, perioperative system 100 may recommend schedule and time for the surgery, pairing of surgeon and anesthesiologist, staff that have worked together on similar cases, predictions for the time for the procedure so that the operating room can be scheduled, etc.

III.J. The Day of Surgery

On the day before surgery, perioperative system 100 may send reminders to patient 10 to ensure that patient 10 arrives on time. Perioperative system 100 has tracked patient 10 to ensure that patient 10 has complied with prep, medication, and prehabilitation instructions, and that health care proxy and advance directive paperwork is in place.

As a final preparation for surgery 270, perioperative system 100 may send a final reminder 268 of any at risk red flags for the surgical team to be aware of.

III.K. Postoperative Recovery, Discharge, Rehab, Therapy, and Follow-Up

After surgery, typically patients stay in recovery 280 for some period of time, typically from hours to days. During that time, hospital 20 is able to keep the patient's information in the patient's medical record 40, 800. But once patient 10 is discharged, the hospital's ability to maintain longitudinal information ends. For example, if patient 10 goes to an emergency room at another hospital for treatment of complications, the hospital where the surgery was done typically does not have access to the other facility's treatment record in a traditional EMR system 40.

After patient 10 leaves the hospital, perioperative system 100 may coordinate patient tracking, follow-up care, post-surgical therapy, and the like. Perioperative system may send reminders of post-op appointments.

Perioperative system 100 may take care of some of the post-operative follow up 290 by sending messages 282 to patient 10. For example, postoperative system may have a set of inquiries and recommendations for orthopedic patients, a set of inquiries and recommendations for cardiac patients, and the like. Inquiries may be tailored to the surgery, or tailored to the specific surgeon.

Perioperative system 100 may send daily check-up messages. For example, perioperative system 100 may ask patient 10 to evaluate pain on a scale of one to ten, and how many pain pills patient 10 has taken. If pain is seven or above, or the number of pills is above the recommended number, then perioperative system 100 may trigger an alert to hospital staff 20 to phone patient 10, to track recovery, monitor opioid use, and the like.

Perioperative system 100 may likewise track the patient's pain control, functional recovery, return to activities of daily living, complications, readmission, emergency room visits, and similar metrics over a period of weeks or months. Perioperative system may gather information relating to criteria and metrics for cost, quality, and patient satisfaction set by public or private payors, such as the criteria set by CMS in its pilot "Comprehensive Care for Joint Replacement Model" described at innovation.cms.gov/initiatives/CJR. If the patient's progress is not as expected, perioperative system 100 may raise an alert with hospital staff 20 to investigate and potentially adjust.

Perioperative system 100 may likewise track the patient's compliance with post-surgical therapy, development of infection, and similar parameters. Perioperative system 100 may request that patient 10 take a photo of the incision site, and facilitate communication back to the hospital 20 in a variety of dimensions.

Perioperative system may ask patient 10 whether certain human caregivers have performed certain tasks; perioperative system 100 may serve as a double check that human medical staff are providing appropriate care. Perioperative system 100 may provide a report to supervisors Perioperative system 100 may ensure that all phases of a surgical episode are longitudinally linked in perioperative database 800 so that costs can be tracked to ensure that hospital 20 can provide accurate cost accounting information to its payors.

This post-surgical communication may be stored in perioperative database 800. This may be especially important when the doctor covering on call for post-surgical follow-up is not the primary surgeon and nursing team.

IV. Closing the Loop: Providing Feedback to Improve Future Health Care

Perioperative system 100 may be programmed to look for patterns among the data, to identify correlations between steps taken early in the surgical episode to cost and outcomes. Perioperative system 100 may identify which patient selection characteristics, preoperative screens, preoperative preparations, and prehabilitation steps are most effective at reducing costs and improving patient benefit. Over time, perioperative system 100 may collect data 298 and analyze it to identify surgeon-specific metrics, patient comorbidities and how they affect costs and outcomes, in order to support decision making (for example, scheduling, staffing, and treatment decisions).

One overall goal of perioperative system 100 is to engage patient 10 more and give them more insight into and control over the entire surgical episode. Various surveys are taken by CMS and also private surveys such as Press Ganey to measure patient satisfaction. Perioperative system 100 may ask the same questions as the surveys, so that hospital 20 can improve its services in ways that are directly measurable.

V. Computer Implementation
V.A. Network and Communications Connections

Figure 5:
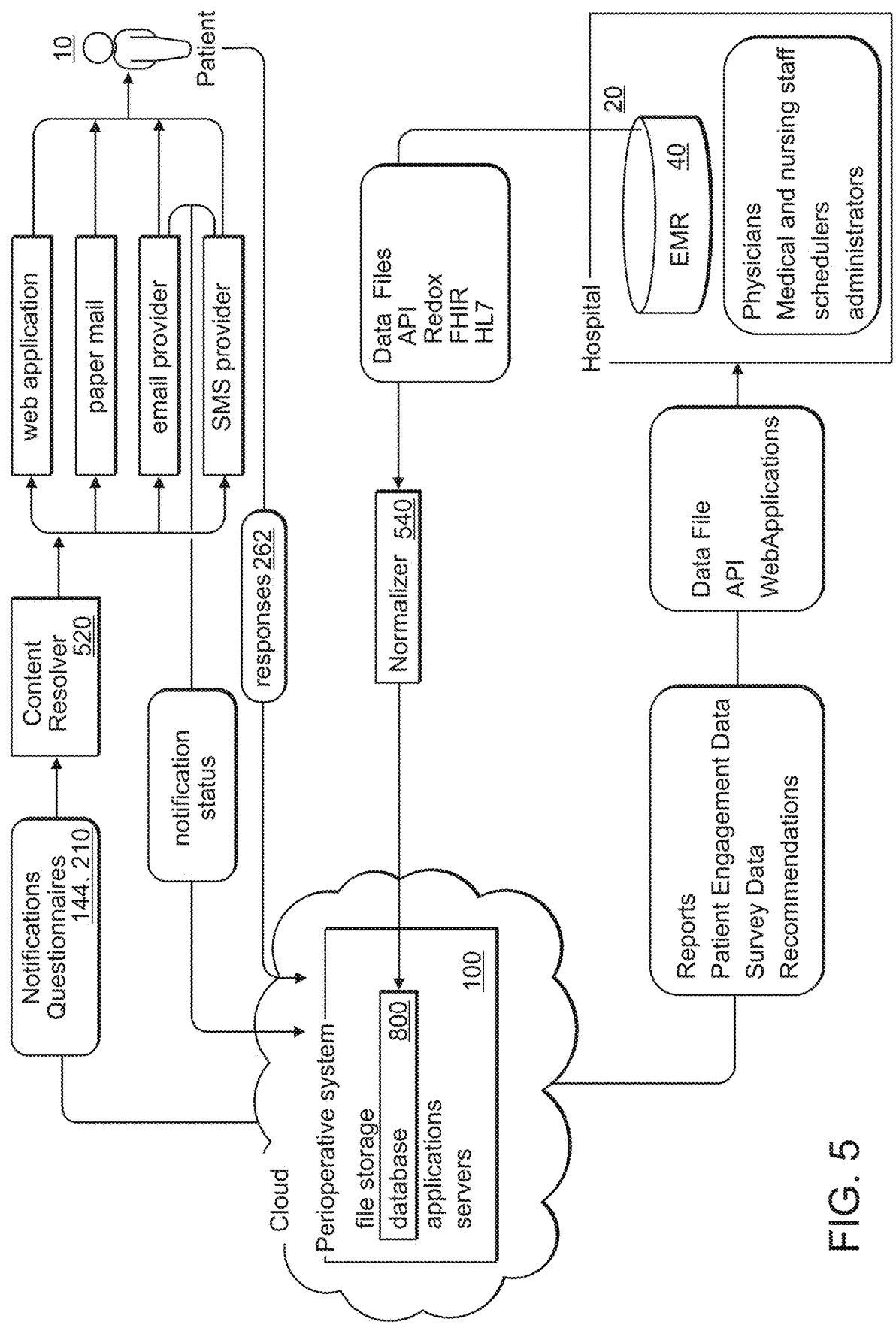

Referring to FIG. 5, perioperative system 100 communicates with two general classes of clients. Hospitals, surgery centers, and healthcare providers 20 allow perioperative system 100 to connect to their on-site EMR databases 40.

From hospital/provider 20, perioperative system 100 collects records relating to patients (demographic, contact information, and medical information), physicians, encounters, scheduling, etc. This data is transferred from hospital/provider 20 via transfer of files (for example, using FTP or variants, once or twice daily, or more often), via Redox, FHIR, and/or HL7 (three standard or widely-used transfer protocols for medical data), and internet web APIs. Because every hospital may store its data in a local, idiosyncratic form, perioperative system 100 may use a normalizer 540 to convert the hospital's data from the form provided by hospital/provider 20 into a uniform, normalized form held within perioperative system 100. Perioperative system 100 flows back to hospital/provider 20 the collection of reports, patient engagement data, survey data, and recommendations discussed in sections I, III, and IV above.

To patients, perioperative system 100 sends questionnaires, notifications, and the like to various delivery providers (for delivery by paper mail, by email, by SMS text, or via web application). For some channels flowing to patient 10, a delivery provider may monitor actual receipt by the recipient, and provide notifications back to perioperative system 100 of delivery success or message delivery failure, for example, if the system attempts to send an SMS message to a disconnected number or to a landline. Perioperative system may rely on delivery services such as Twilio for delivery of SMS messages, and SendGrid® for email messages, and to provide notifications to the hospital/provider 20 for delivery failure.

In this path, content resolver 520 may be responsible for accepting basic "form letter" standard messages, and populating each one with specific data, such as patient name, appointment date and time, and the like, to tailor the messages to the specific event for the specific patient. Content resolver 520 may adjust appointment arrival times for whether patient 10 is to receive general or local anesthesia, whether patient 10 has outstanding paperwork requirements, and the like.

From patient 10, perioperative system 100 may receive responses 262 from the patient in response to earlier messages. Likewise, the patient-to-system path may permit patient to provide unsolicited content to perioperative system 100, for example, to report an unexpected event, a photograph of an incision site, a narrative text description of some event, and the like. Information to patients flows circularly from perioperative system 100 to patient 10 and back, to keep patient 10 moving through the care episode, to navigate patient 10 to the most-helpful point in the system's web site, to educate patient 10, to help patient 10 arrive at appointments on time, to help avoid late cancels, and to collect information that may feed machine learning algorithms in perioperative system 100.

V.B. Patient Enrollment

Figure 6:
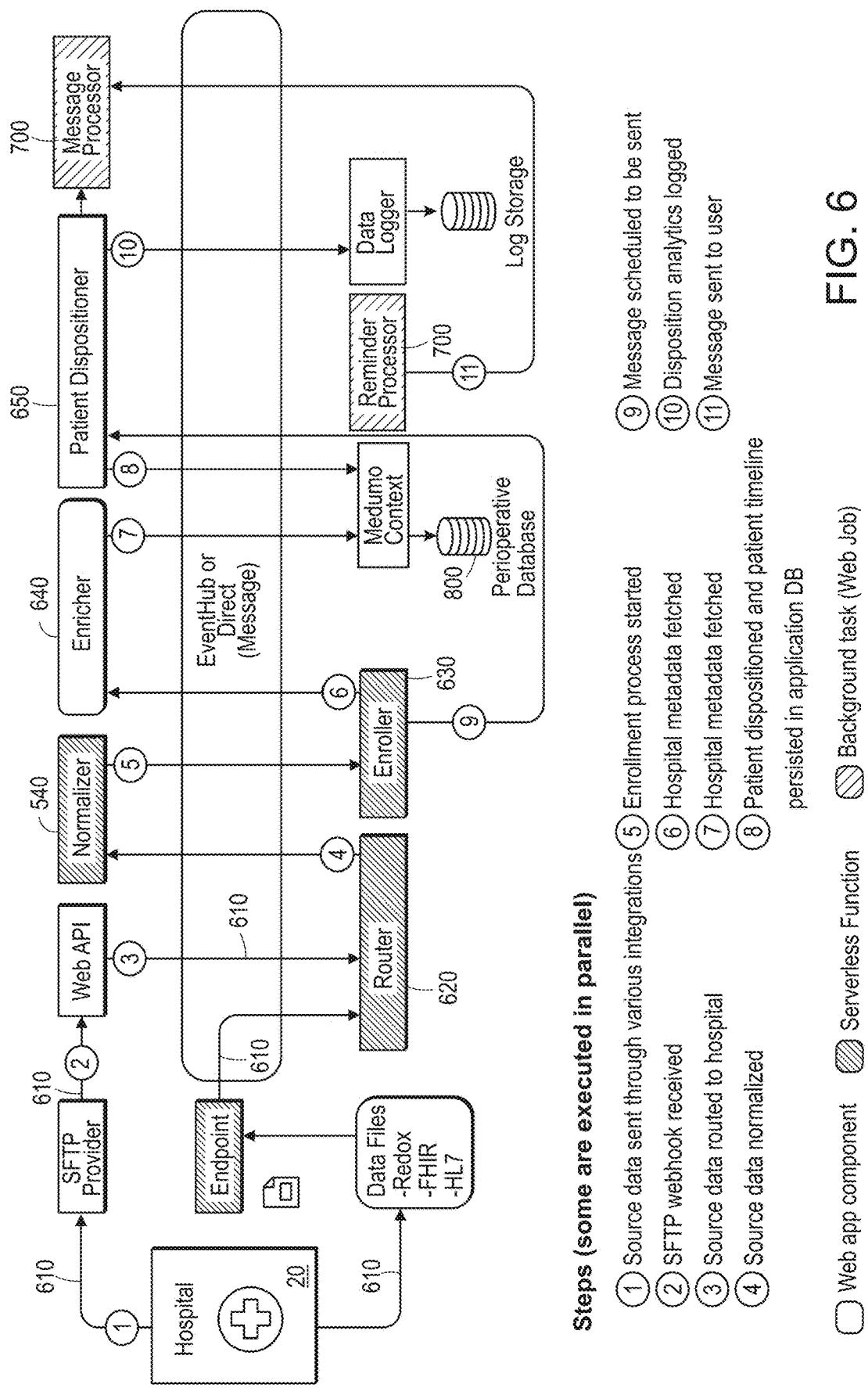

Referring to FIG. 6, when a hospital/provider 20 receives a referral for a new patient, hospital/provider 20 may trigger perioperative system 100 to enroll a new patient into the perioperative database 800, creating either a normalized record to track the hospital's record. Hospital 20 collects various patient data into an integrated package to send (arcs 610) to perioperative system 100, and transmits it, e.g., by SFTP (secure FTP), web API or another data transfer protocol. Router 620 examines packet headers or other information to identify which hospital/provider sent the patient package.

Normalizer 540 converts the data from the hospital-specific form in which it's received into a normalized, common form used internally to perioperative system 100. For example, because data as basic as phone numbers, name order (first middle last, or last first middle), addresses, and the like are stored in different forms in various hospital EMRs 40, normalizer 540 converts all names into a uniform, normalized form to be used within perioperative system 100. In some cases, one hospital may use Epic®, another Cerner®, and another Meditech, and the patient's primary care physician may use eClinicalWorks®, and normalizer 540 will convert the data it receives from all of them into the common internal form used by perioperative database 800. In some cases, normalizer 540 builds perioperative database 800 as a shadow copy of hospital EMR 40, by translating each record received from hospital EMR 40 into the normalized form used by perioperative system 100. In other cases, normalizer 540 may avoid duplicate storage of data, and operate as an on-demand translator, translating in two directions: perioperative database 800 may be constructed as a series of associations between records in the hospital's own EMR database 40, and each time perioperative system 100 calls for data, normalizer 540 calls for that data from hospital EMR 40 and translates it to the normalized form, and when perioperative system 100 wants to write the data, normalizer 540 converts that to a write into hospital EMR in the form stored by hospital EMR 40.

Enroller 630 pulls data from perioperative database 800 to validate and supplement the patient data received from hospital/provider 20. Enricher 640 queries perioperative database 800 to ask whether this specific patient already exists in perioperative database 800, and ascertains what information is already known about this patient. Is patient 10 already known to perioperative database 800? What pathways have already been assigned? Is this package from hospital/provider an update to an existing pathway? Is this a request to open a new pathway? Is this a request to cancel an existing pathway? Is this a creation of a new encounter, a rescheduling, or a cancellation? Based on that information, enricher 640 and dispositioner 650 enrich the normalized data for the patient, and fills in and populates that patient record with information to permit perioperative system to begin reasoning about patient 10, and to begin offering recommendations. The system maintains a database transaction log of its own actions. Via reminder/message processors 700, various messages may be sent to persons at hospital/provider 20, or to patient 10, notifying of appointments, cancelations, reschedules, changes in recommended action, and the like.

Some components shown in FIG. 6 may be implemented as "serverless functions," in which the software application is hosted in the cloud, and only instantiated when some event occurs that requires the function to operate. A "serverless function" is typically stateless between invocations; all data managed by a serverless function is committed to permanent storage. Other components of FIG. 6 may be implemented as "background processes" that is always running and monitoring for work, and maintains state across invocations.

V.C. Reminders and Notifications

Figure 7A:
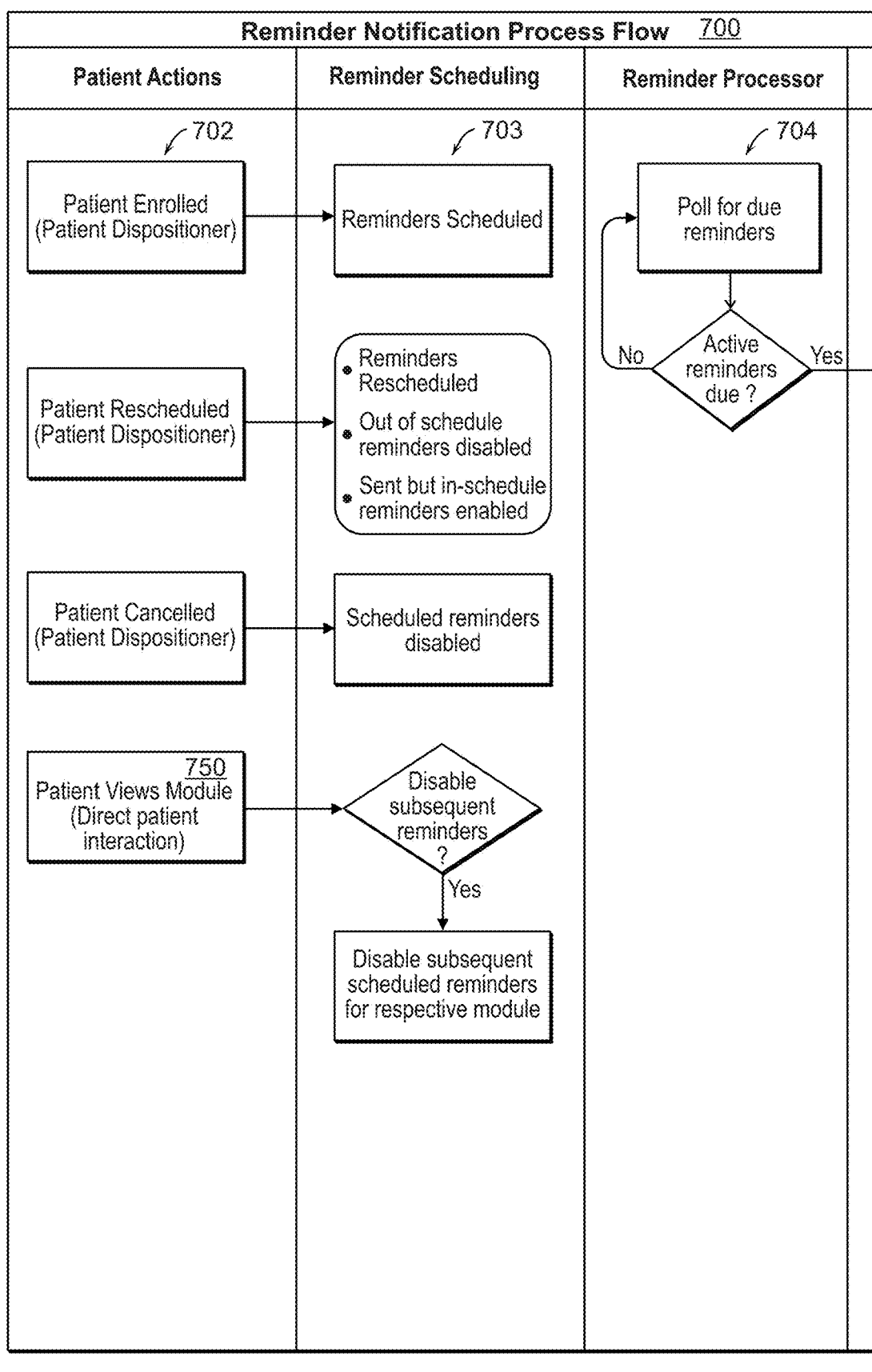
Figure 7A:
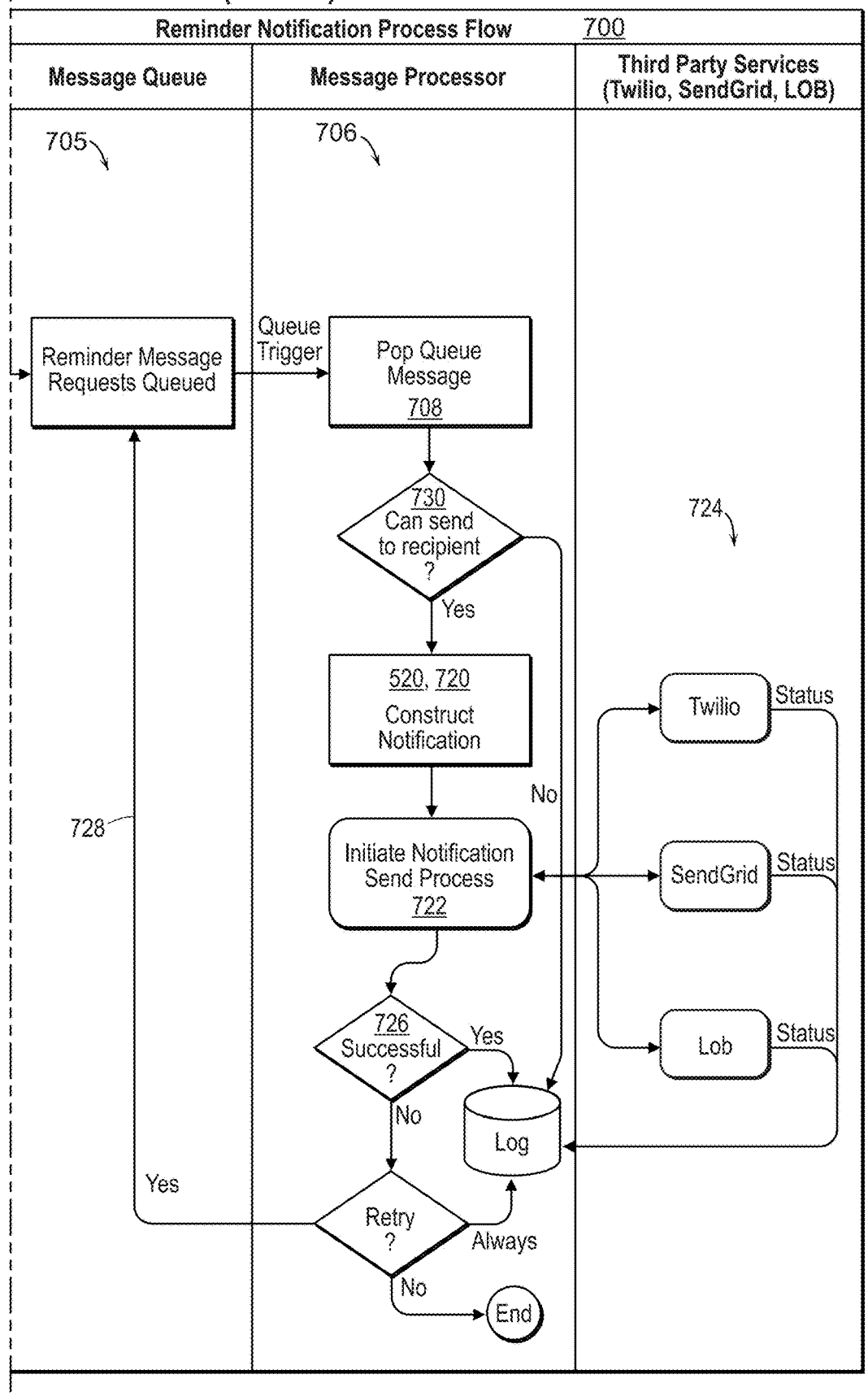
Figure 7B:
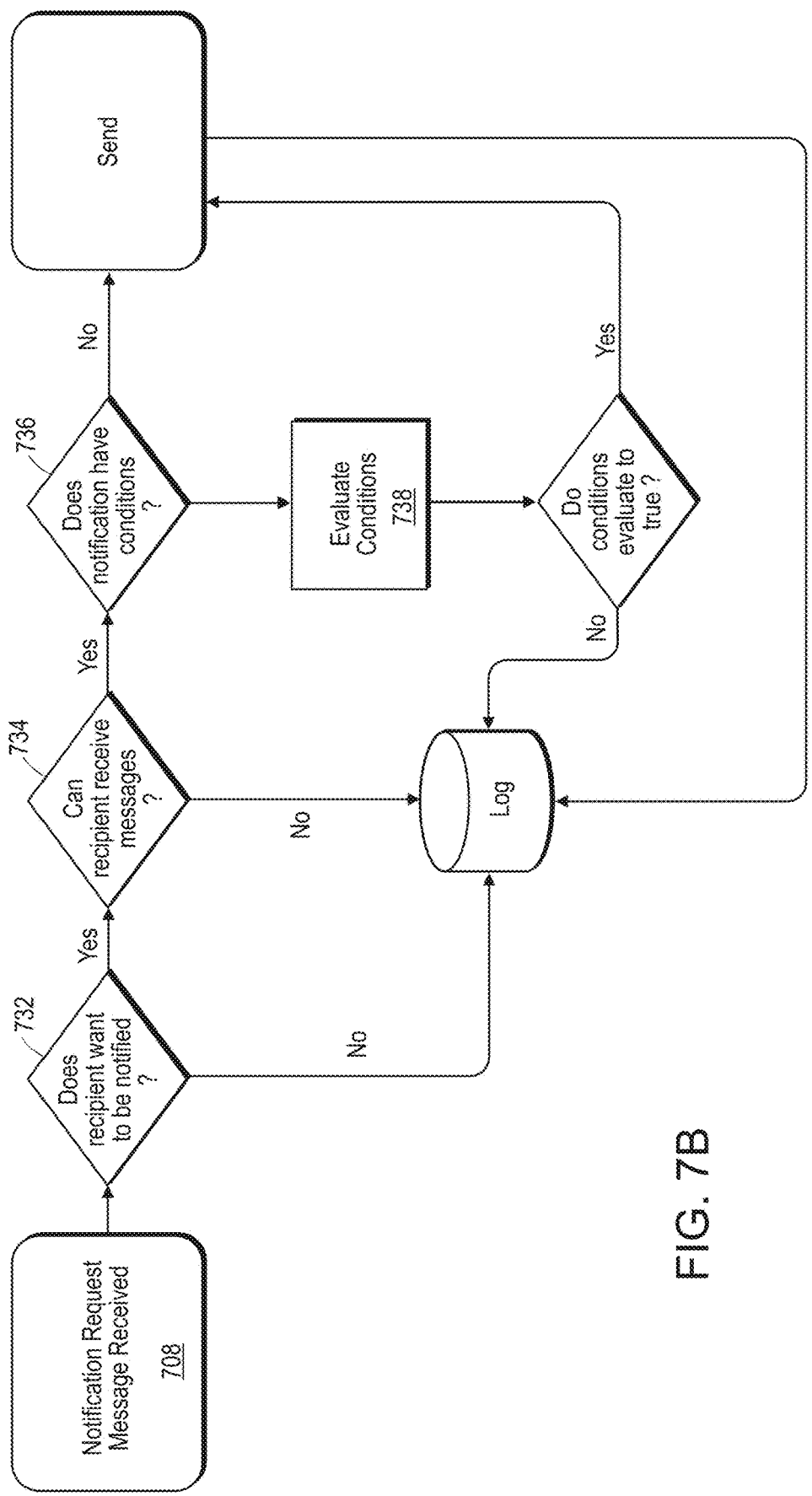

Referring to FIGS. 7A and 7B, after a patient is enrolled or an update is received by perioperative system 100 from hospital/provider (see FIG. 6), perioperative system 100 may determine to send various notifications and reminders, or to update various milestone dates for various actions. For example, if an appointment is moved, the queue of messages may be updated. If the update affects substantive treatment decisions, perioperative system may send notifications of new appointments, new recommendations, etc.

Reminder/notification system 700 may be structured as a series of stages. For example, stage 702 may be triggered when a patient takes an action. FIG. 7A shows four potential patient actions that trigger further action by the reminder/notification processor 700. Stage 703 may be the first action taken, to queue a request for a reminder, to be processes later. Stage 704 may be a polling system, a process that periodically wakes up (for example, when system load is otherwise low) and checks to see whether any reminder actions are queued to be taken now. Stage 705 may be a processor that acts on a queue of reminders/notifications to be sent. Stage 706 may be a message processor, that takes an action off the message queue (step 708), checks to make sure that a reminder/notification is appropriate (step 730), constructs the reminder/notification using content resolver (520, step 720), decides which channel is most appropriate for this message (SMS, email, or other) (step 722) and triggers the appropriate/corresponding delivery service (step 724), checks for a success notification (step 726), and if no message success notification is received, initiates a retry (step 728).

FIG. 7B elaborates some of the logic for sending reminders and notification, specifically some of the logic to determine what to send and when to send it (step 730). If a message is waiting in the message queue (708), the system evaluates whether the person (patient or persona t hospital/provider) has given consent of enabled a messaging preference (step 732). Then, perioperative system 100 may evaluate whether the system has a valid phone number, email address, or other contact information (step 734). If so, perioperative system 100 may evaluate (steps 736, 738) whether the reminder/notification has conditions, and whether those conditions are currently satisfied, such as conditions relevant to the specific pathway this patient is on, and whether patient 10 has previously checked this content. If that the condition evaluates to true, then reminder/notification system 700 may send the message. Reminder/notification system 700 may maintain a log of all decisions and messages sent.

Returning to FIG. 7A, reminders may be "chained." For example, if hospital/provider sends information to patient 10 for the patient's review, there may be a chain of reminders for immediate, one day, two days, three days, five days, eight days, etc., on a schedule configurable by hospital/provider 20. At box 750, once patient 10 reviews the information once and acknowledges, the chain of reminders can be terminated.

Notification messages and reports may flow to personnel at hospital/provider through either the same reminder/notification process as is used for patients, via a channel that leads back through the hospital's EMR system 40, or though another channel. Reports may include:

An unreachable/message failure report for messages that did not go through to patient 10, perhaps including all known contact information for patient 10, so that a human can explore alternatives channels for reaching patient 10.

The level of the patient's engagement with messages, for example, time delays before messages are read, the amount of time patient 10 spends, whether patient 10 responds and how quickly, etc.

Survey responses analyzed to evaluate specific at risk characteristics such as frailty, mental competence, risk factors such as diabetes or opioid abuse, general levels of timeliness for arrival at appointments.

An indication of patients that are likely to require additional personal guidance when they arrive for an appointment.

V.D. Patient Timelines and Perioperative Database

Figure 8A:
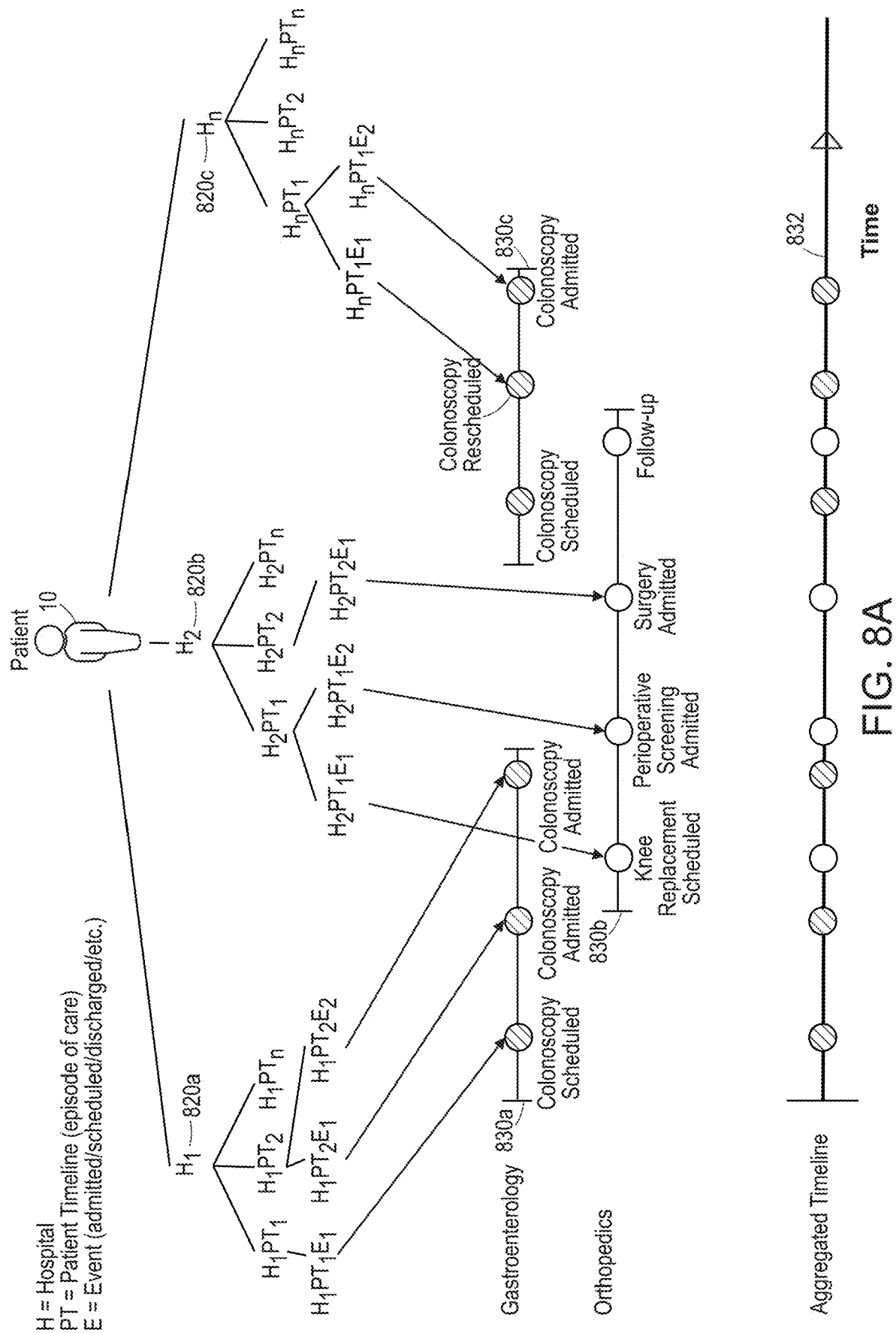
FIGS. 8A and 8B are data structure diagrams.

Referring to FIG. 8A, perioperative database 800 may collect information from multiple hospitals and providers 20, and integrate that information into consolidated episodes of care, and an overall patient life cycle. This integrated, holistic view may allow treating physicians to understand patient 10 better, to avoid adverse interactions, avoid risks relating to underlying co-morbidities, and to stratify various risks.

In FIG. 8A, a single patient 10 has received treatment at three hospitals 820*a*, 820*b*, and 820*c* over several years. At hospital $H_1$, patient 10 received a first colonoscopy. At hospital $H_2$, the patient received a knee replacement. At hospital $H_3$, patient 10 received a second colonoscopy. These three episodes are shown in the three bubble timelines 830*a*, 830*b*, 830*c*. In addition, at the bottom of FIG. 8A, perioperative system 100 may show an integrated timeline 832 with all episodes in temporal order. A traditional EMR system 40 does not readily allow hospital personnel to track any of these three episodes in a longitudinal way, let alone the patient's entire integrated history.

Various heuristics from the encounter records may be used to collect the encounters of a single episode. For all encounters at a single hospital, all will be associated with the same patient. The patient's medical records at different hospitals may be correlated with each other based on social security number, or two medical records with a similar name having the same telephone number and address, and the like. Encounter records may be associated with each other into an episode based on CMS fee codes from related category (a knee surgery billing code is unlikely to be the same episode as a colonoscope billing code, but a colonoscopy and diverticular surgery likely are related), same physician, and the like.

Figure 8B:
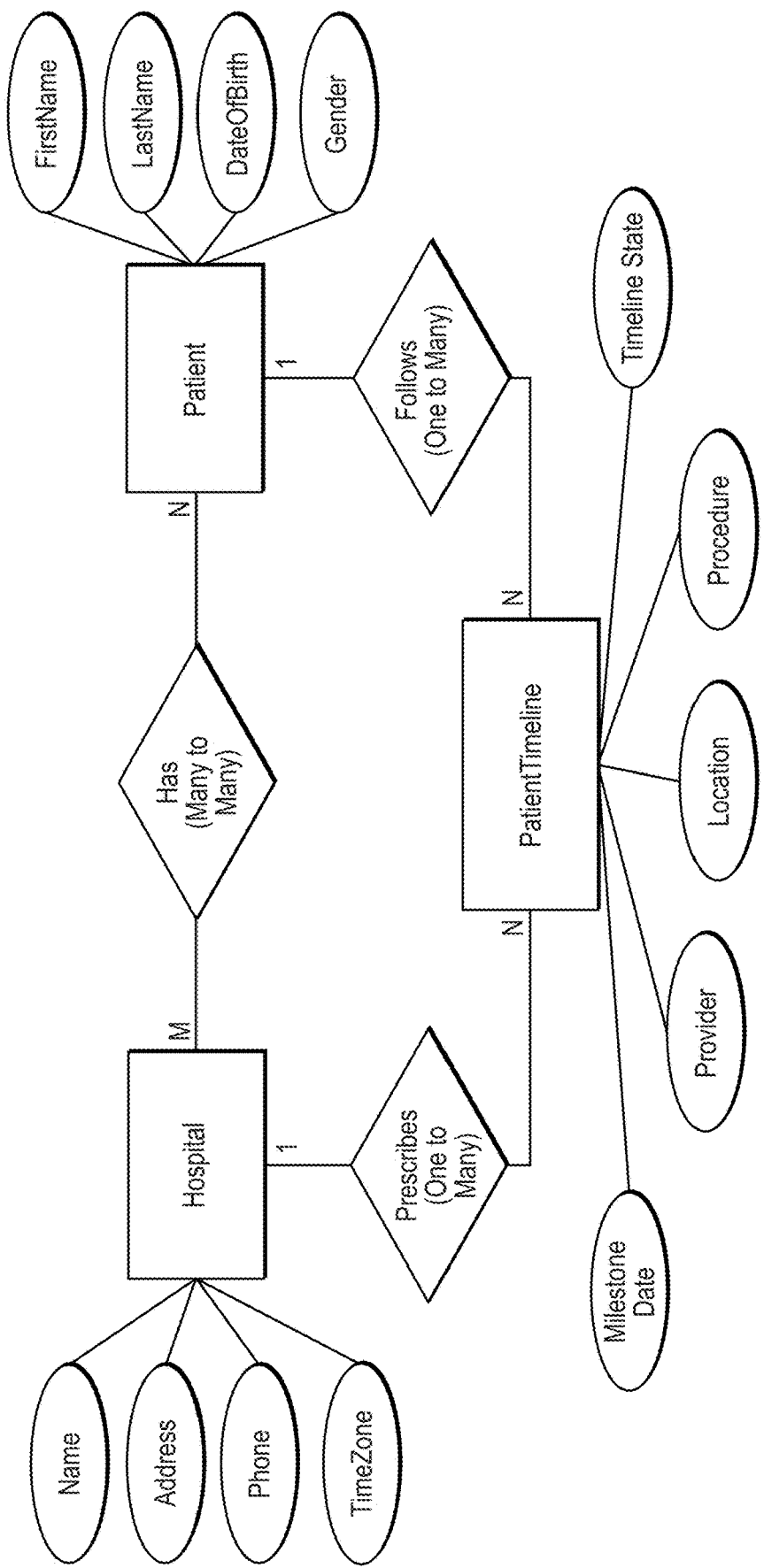

FIG. 8B is a depiction of a database schema, shown as an entity relationship diagram. A hospital may have a name, address, phone number, and time zone. A patient may have a first name, last name, date of birth, and gender. Hospitals and patients are joined by many-to-many connections. Each patient has one or more episodes with one or more hospitals, again in many-to-many relationships. Each episode has several encounters, each of which has a date, provider, location, and procedure, several milestones which in turn have dates, reminders, and completion statuses.

V.E. Other Computer Hardware Concerns

Some steps in perioperative workflow may occur out of the sequence presented above, or in parallel. For example, aspects of post-surgical treatment may be planned before surgery begins, or while patient 10 is still in surgery. Similarly, from any particular party's perspective, the steps in their role or function may occur in parallel with the steps of other parties. For example, the steps for an operating nurse may occur, at least in part, in parallel with those of a surgeon and an anesthesiologist.

Various processes described herein may be implemented by appropriately programmed general purpose computers, special purpose computers, and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in one or more computer programs, one or more scripts, or in other forms. The processing may be performed on one or more microprocessors, central processing units (CPUs), computing devices, microcontrollers, digital signal processors, or like devices or any combination thereof. Programs that implement the processing, and the data operated on, may be stored and transmitted using a variety of media. In some cases, hard-wired circuitry or custom hardware may be used in place of, or in combination with, some or all of the software instructions that can implement the processes. Algorithms other than those described may be used.

Programs and data may be stored in various media appropriate to the purpose, or a combination of heterogenous media that may be read and/or written by a computer, a processor or a like device. The media may include non-volatile media, volatile media, optical or magnetic media, dynamic random access memory (DRAM), static ram, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge or other memory technologies. Transmission media include coaxial cables, copper wire and fiber optics, including the wires that comprise a system bus coupled to the processor.

Databases may be implemented using database management systems or ad hoc memory organization schemes. Alternative database structures to those described may be readily employed. Databases may be stored locally or remotely from a device which accesses data in such a database. The overall database may include a single database system, or may be built up from multiple separate or integrated databases, at least some of which may be distributed. The database may be implemented in any manner. If the overall database is made up of multiple underlying databases, the underlying databases may be implemented in different manners.

In some cases, the processing may be performed in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium® or Centrino™ processor, that are adapted to communicate with the computer. Any number and type of devices may be in communication with the computer.

A server computer or centralized authority may or may not be necessary or desirable. In various cases, the network may or may not include a central authority device. Various processing functions may be performed on a central authority server, one of several distributed servers, or other distributed devices For clarity of explanation, the above description has focused on a representative sample of all possible embodiments, a sample that teaches the principles of the invention and conveys the best mode contemplated for carrying it out. The invention is not limited to the described embodiments. Well known features may not have been described in detail to avoid unnecessarily obscuring the principles relevant to the claimed invention. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed alternatives, variations, modifications, and equivalents are within the literal scope of the following claims, and others are equivalent. The claims may be practiced without some or all of the specific details described in the specification. In many cases, method steps described in this specification can be performed in different orders than that presented in this specification, or in parallel rather than sequentially, or in different computers of a computer network, rather than all on a single computer.

The invention claimed is:
1. A method, comprising:
  storing a library of electronic pathways for treatment of patients, each pathway being a standardized sets of tasks, medications, and/or interventions for an identified population of patients and including orders, each pathway and its orders being neutral as to patient and schedule;
  automatically, as part of pre-surgical evaluation by a hospital, in response to receiving a referral of a patient to a physician for a multi-encounter medical procedure, retrieving EMR information from a patient's electronic medical record (EMR) stored in an electronic medical record system, the patient's EMR storing patient encounters as separate patient encounter records in which no patient encounter record is linked with any other patient encounter record;

evaluating the EMR information to identify an at risk condition for the patient;

assembling a database record reflecting patient encounters of the patient and assembling the patient encounters into a plurality of medical episode records for the patient, the medical episode records relating to corresponding medical conditions of the patient, each medical episode record storing information relating to patient encounters relating to treatment of the corresponding medical condition;

storing the database record in a database of medical episode records, designed to permit longitudinal retrieval of patient encounters of a medical episode record;

in response to the EMR evaluation determining that the patient is possibly at risk, posing a questionnaire to all patients for specified classes of procedures, the patients meeting specified criteria for possible risk, the questionnaire being specifically diagnostic for the at risk condition and/or appropriateness of care preferences of the patient, and obtaining answers from the patient to questions of the questionnaire;

evaluating the information from the patient's EMR and the answers from the patient to the questions of the questionnaire together to evaluate risk characteristics of the patient and/or appropriateness of care preferences of the patient;

if the evaluating of the information from the patient's EMR and the answers from the patient to the questions of the questionnaire together indicates the at risk condition for the patient, recommending to medical staff a pathway chosen from among the library:

determining, based on the evaluating of the information from the patient's EMR and the answers from the patient to the questions of the questionnaire together, whether the patient is eligible for a telephone preoperative evaluation;

based on the evaluating of the EMR information and questionnaire answers together, recommending to medical staff at least one pathway template to be implemented by the medical staff in the patient's care, from among a library of pathway templates, the pathway templates being standardized sets of tasks, medications, and/or interventions for an identified population of patients, each pathway template being neutral as to patient and schedule and including orders;

instantiating the recommended pathway template to create at least one pathway to be implemented for the patient by populating the orders of the recommended pathway template with the EMR information to create instantiated orders for the patient, the instantiating of at least one pathway to be implemented further including determining, based on the evaluating of the EMR information and questionnaire answers together, whether the patient is eligible for a telephone preoperative evaluation or an in-person preoperative evaluation wherein an adverse answer to any of the questions that are specifically diagnostic for the at risk condition indicates the patient must have an in-person preoperative evaluation;

performing a multi-encounter medical procedure on the patient utilizing the at least one pathway to be implemented and storing patient encounter records of the multi-encounter medical procedure in the patient's EMR;

linking the patient encounter records of the multi-encounter medical procedure stored in the patient's EMR into a longitudinally-linked episode; and storing the longitudinally-linked episode in the patient's EMR as a connective record that links to the patient encounter records of the multi-encounter medical procedure.

2. The method of claim 1, wherein the multi-encounter medical procedure comprises a multi-encounter perioperative episode.

3. The method of claim 1, wherein:
the at risk condition comprises frailty and the question of the questionnaire include a question of whether the patient is able to lie flat comfortably.

4. The method of claim 1, wherein:
the at risk condition comprises postoperative delirium.

5. The method of claim 1, wherein:
the risk characteristic identified by evaluating the EMR information and questionnaire answers is extended inpatient rehabilitation or non-home discharge.

6. The method of claim 1, wherein:
the appropriateness of care preference identified by evaluating the EMR information and questionnaire answers is risk that the patient may have an atypical risk preference; and
the recommendation is to interview the patient and to counsel for appropriate treatment.

7. The method of claim 1, further comprising the step of:
adjusting further questions to be asked of the patient based at least in part on past questionnaire answers.

8. An apparatus, comprising:
one or more computers, each having a processor and a memory, the memory having stored therein instructions programmed to cause the one or more computers to maintain an electronic medical record (EMR) system that stores patient encounters as separate fee-for-service billable patient encounter records in which no patient encounter record is linked with any other patient encounter record and to, in response to receiving a referral of a patient for a multi-encounter medical procedure:

store a library of electronic pathways for treatment of patients, each pathway being a standardized sets of tasks, medications, and/or interventions for an identified population of patients and including orders, each pathway and its orders being neutral as to patient and schedule;

automatically, as part of pre-surgical evaluation by a hospital, in response to receiving a referral of a patient to a physician for a multi-encounter medical procedure, retrieve EMR information about a patient from the patient's EMR stored in the EMR system;

assemble a database record reflecting patient encounters of the patient and assembling the patient encounters into a plurality of medical episode records for the patient, the medical episode records relating to corresponding medical conditions of the patient, each medical episode record storing information relating to patient encounters relating to treatment of the corresponding medical condition;

store the database record in a database of medical episode records, designed to permit longitudinal retrieval of patient encounters of a medical episode record;

in response to the EMR evaluation determining that the patient is possibly at risk, pose a questionnaire to all patients for specified classes of procedures, the patients meeting specified criteria for possible risk, the questionnaire being specifically diagnostic for the at risk condition and/or appropriateness of care preferences of the patient, and obtaining answers from the patient to questions of the questionnaire;

evaluate the information from the patient's EMR and the answers from the patient to the questions of the questionnaire together to evaluate risk characteristics of the patient and/or appropriateness of care preferences of the patient:

if the evaluating of the information from the patient's EMR and the answers from the patient to the questions of the questionnaire together indicates the at risk condition for the patient, recommend to medical staff a pathway chosen from among the library:

determine, based on the evaluating of the information from the patient's EMR and the answers from the patient to the questions of the questionnaire together, whether the patient is eligible for a telephone preoperative evaluation;

based on the evaluation of the EMR information and the patient's answers together, recommend to medical staff a pathway template to be implemented by the medical staff to perform the multi-encounter medical procedure on the patient, from among a library of pathway templates, the pathway templates being standardized sets of tasks, medications, and/or interventions for an identified population of patients, each pathway template being neutral as to patient and schedule, instantiate the recommended pathway template to create an instantiated pathway to be implemented for the patient based on the evaluation of the EMR information and the patient's answers together, the instantiated pathway to be implemented including a determination, based on the evaluation of the EMR information and the patient's answers together, of whether the patient is eligible for a telephone preoperative evaluation or an in-person preoperative evaluation; and link patient encounter records of the multi-encounter medical procedure generated by implementation of the instantiated pathway and stored in the patient's EMR into a longitudinally-linked episode, and store the longitudinally-linked episode in the patient's EMR as a connective record that links to the patient encounter records of the multi-encounter medical procedure.

9. The apparatus of claim 8, the instructions being further programmed to cause the computer(s) to:
in response to receiving the referral of a patient to a physician for a multi-encounter medical procedure, evaluate the patient's EMR for conditions suggesting the possibility of an at risk condition for the patient,
in response to the EMR evaluation determining that the patient is possibly at risk for the at risk condition, including in the questionnaire one or more questions that are specifically diagnostic for the at risk condition;
wherein an adverse answer to any of the one or more questions that are specifically diagnostic for the at risk condition indicates the patient must have an in-person preoperative evaluation.

10. The method of claim 8, wherein:
the instantiated pathway relates to reducing risk of postoperative delirium.

11. The method of claim 8, wherein:
the instantiated pathway relates to reducing risk of extended inpatient rehabilitation or non-home discharge.

12. The method of claim 8, wherein:
the instantiated pathway relates to reducing risk of anemia.

13. The method of claim 8, wherein:
the instantiated pathway relates to reducing risk of diabetes.

14. The method of claim 8, wherein:
the instantiated pathway relates to improving robustness in advance of surgery.

15. The method of claim 8, further comprising the step of:
by the one or more computers, adjusting further questions to be asked of the patient based at least in part on past questionnaire answers.

16. A method, comprising:
storing a library of electronic pathways for treatment of patients, each pathway being a standardized sets of tasks, medications, and/or interventions for an identified population of patients and including orders, each pathway and its orders being neutral as to patient and schedule;

automatically, as part of pre-surgical evaluation by a hospital, in response to receiving a referral of a patient to a physician for a multi-encounter medical procedure, retrieving information from a patient's electronic medical record (EMR) of the patient stored in an electronic medical record system, the patient's EMR storing patient encounters as separate patient encounter records in which no patient encounter record is linked with any other patient encounter record;

evaluating the information retrieved from the patient's EMR for conditions suggesting the possibility of an at risk condition for the patient, at least one at risk condition under evaluation being frailty;

assembling a database record reflecting patient encounters of the patient and assembling the patient encounters into a plurality of medical episode records for the patient, the medical episode records relating to corresponding medical conditions of the patient, each medical episode record storing information relating to patient encounters relating to treatment of the corresponding medical condition;

storing the database record in a database of medical episode records, designed to permit longitudinal retrieval of patient encounters of a medical episode record;

in response to the EMR evaluation determining that the patient is possibly at risk, posing a questionnaire to all patients for specified classes of procedures, the patients meeting specified criteria for possible risk, the questionnaire being specifically diagnostic for the at risk condition and/or appropriateness of care preferences of the patient, and obtaining answers from the patient to questions of the questionnaire, the questionnaire including at least a question of whether the patient is able to lie flat comfortably;

evaluating the information from the patient's EMR and the answers from the patient to the questions of the questionnaire together to evaluate risk characteristics of the patient and/or appropriateness of care preferences of the patient;

if the evaluating of the information from the patient's EMR and the answers from the patient to the questions of the questionnaire together indicates the at risk condition for the patient, recommending to medical staff a pathway chosen from among the library;

determining, based on the evaluating of the information from the patient's EMR and the answers from the patient to the questions of the questionnaire together, whether the patient is eligible for a telephone preoperative evaluation;

based on the evaluating of the information from the patient's EMR and the answers from the patient to the questions of the questionnaire together, recommending to the medical staff, at least one pathway from the library relating to the at risk condition to be implemented by the medical staff in the patient's care, the at least one pathway to be implemented including whether the patient is eligible for a telephone preoperative evaluation or an in-person preoperative evaluation;

instantiating the selected pathway and its orders as orders for the identified patient in a database of orders, and populating the instantiated orders with data to particularize the instantiated orders to the patient and the patient's medical condition, the data obtained by a query to the patient's EMR;

performing a medical procedure on the patient utilizing the selected pathway;

linking patient encounter records of the multi-encounter medical procedure stored in the patient's EMR into a longitudinally-linked episode; and storing the longitudinally-linked episode in the patient's EMR as a connective record that links to the patient encounter records of the multi-encounter medical procedure.

* * * * *